Figure 8:
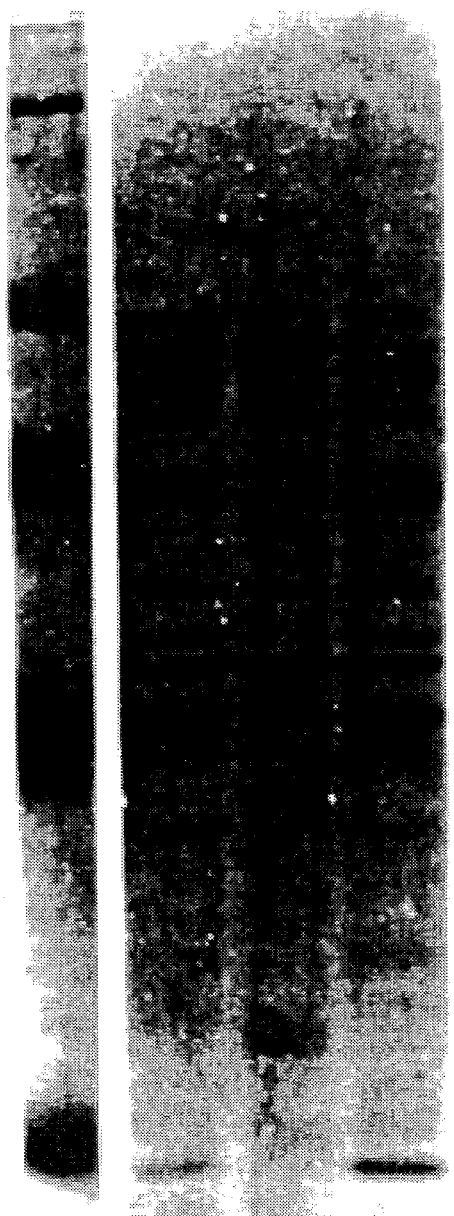

United States Patent [19]

Kuner et al.

[11] Patent Number: 5,459,048
[45] Date of Patent: Oct. 17, 1995

[54] DNA ENCODING 85KD POLYPEPTIDE USEFUL IN DIAGNOSIS OF MYCOPLASMA INFECTIONS IN ANIMALS

[75] Inventors: Jerry Kuner, Longmont; Christine Ko, Boulder, both of Colo.

[73] Assignee: Synergen, Inc., Boulder, Colo.

[21] Appl. No.: 153,495

[22] Filed: Nov. 17, 1993

Related U.S. Application Data

[63] Continuation of Ser. No. 962,075, Oct. 16, 1992, abandoned, which is a continuation of Ser. No. 502,640, Apr. 2, 1990, abandoned, which is a continuation-in-part of Ser. No. 196,891, May 18, 1988, abandoned, which is a continuation of Ser. No. 889,153, Jul. 25, 1986, abandoned.

[51] Int. Cl.$^6$ .......................... C07K 15/28; C07K 15/00; C12P 21/08
[52] U.S. Cl. .................. 435/69.3; 435/70.21; 435/320.1; 424/264.1; 424/168.1; 536/23.7; 530/386.4; 530/389.5
[58] Field of Search ................................ 435/69.3, 70.21, 435/240.27, 320.1, 870; 424/88, 92, 264.1, 168.1; 935/15; 530/388.4, 389.5, 403; 536/23.7

[56] References Cited

U.S. PATENT DOCUMENTS 4,894,332  1/1990  Schaller et al. ........................ 435/69.3

FOREIGN PATENT DOCUMENTS 0283840   9/1988  European Pat. Off. .
WO88/00977  2/1988  WIPO .

OTHER PUBLICATIONS

Beltz et al, Methods in Enzymology, vol. 100:266–285 (1983) "Isolation of Mutigem Families . . . by Hybridization . . .".

Primary Examiner—David L. Lacey
Assistant Examiner—T. Michael Nisbet
Attorney, Agent, or Firm—Finnegan, Henderson, Farabow, Garrett & Dunner

[57] ABSTRACT

A class of polypeptides useful in an in vitro diagnosis of Mycoplasma infection in animals is disclosed. These polypeptides are also capable of inducing an immune response in swine which were previously not exposed to Mycoplasma. Recombinant DNA methods for the production of these polypeptides and certain phage vectors and DNA sequences useful in these methods are also disclosed. Methods of vaccinating animals utilizing a vaccination composition which includes these polypeptides is also disclosed.

6 Claims, 39 Drawing Sheets

```
                                    TC3 coupler
                        ┌─────────────────────────────────────┐
                        Bam HI
                        GGATCCGATCTTGGAGGATGAT TAA ATG
                                                          Met N-Terminus of Protein C
                    │                                    Eco RI
DNA modified        caG cag caG gaA gca aaC tcC ac┄┄┄┄┄t
DNA original        caa cag caa gag gca aat tca act aat tct
Amino Acid Sequence Gln Gln Gln Glu Ala Asn Ser Thr Asn Ser agC ccG act agC ccG agc ccG agC ccG act
                    agt cca ┄┄┄ cca agc cct agt cca ┄┄┄
                    Ser Pro Thr Ser Pro Ser Pro Ser Pro Thr
                            Spe I                     Spe I
```

FIG. 1A

```
                    10          20          30          40          50          60
                     *           *           *           *           *           *
AA  AAA TTA GAT CTT AAT CAG ATC GAA GAC GGC ATC TTT AGA CGA GCT AAG GCA ATT AAA
     K   L   D   L   N   Q   I   E   D   G   I   F   R   R   A   K   A   I   K 70          80          90         100         110         120
               *           *           *           *           *           *
CTT ATA GAT AAA TCA AAC AAT AAC CAA GGA ATT TAT TTT TCC TTT AAT AAC CAG TTT
 L   I   D   K   S   N   N   N   Q   G   I   Y   F   S   F   N   N   Q   F 130         140         150         160         170         180
               *           *           *           *           *           *
TTA AAA TTC CAC GAA CGT GGA TGG ATG TCA ACT TTA TAT TTA CCT AAT GAG GCA AAA ACT
 L   K   F   H   E   R   G   W   M   S   T   L   Y   L   P   N   E   A   K   T 190         200         210         220         230         240
               *           *           *           *           *           *
AAA TTA GCA GAT TAT CAA AAT CTT TTA TCC GCT GGG ATA AGC GAT ACC AAG ATT TTT AGT
 K   L   A   D   Y   Q   N   L   L   S   A   G   I   S   D   T   K   I   F   S
```

FIG. 1B

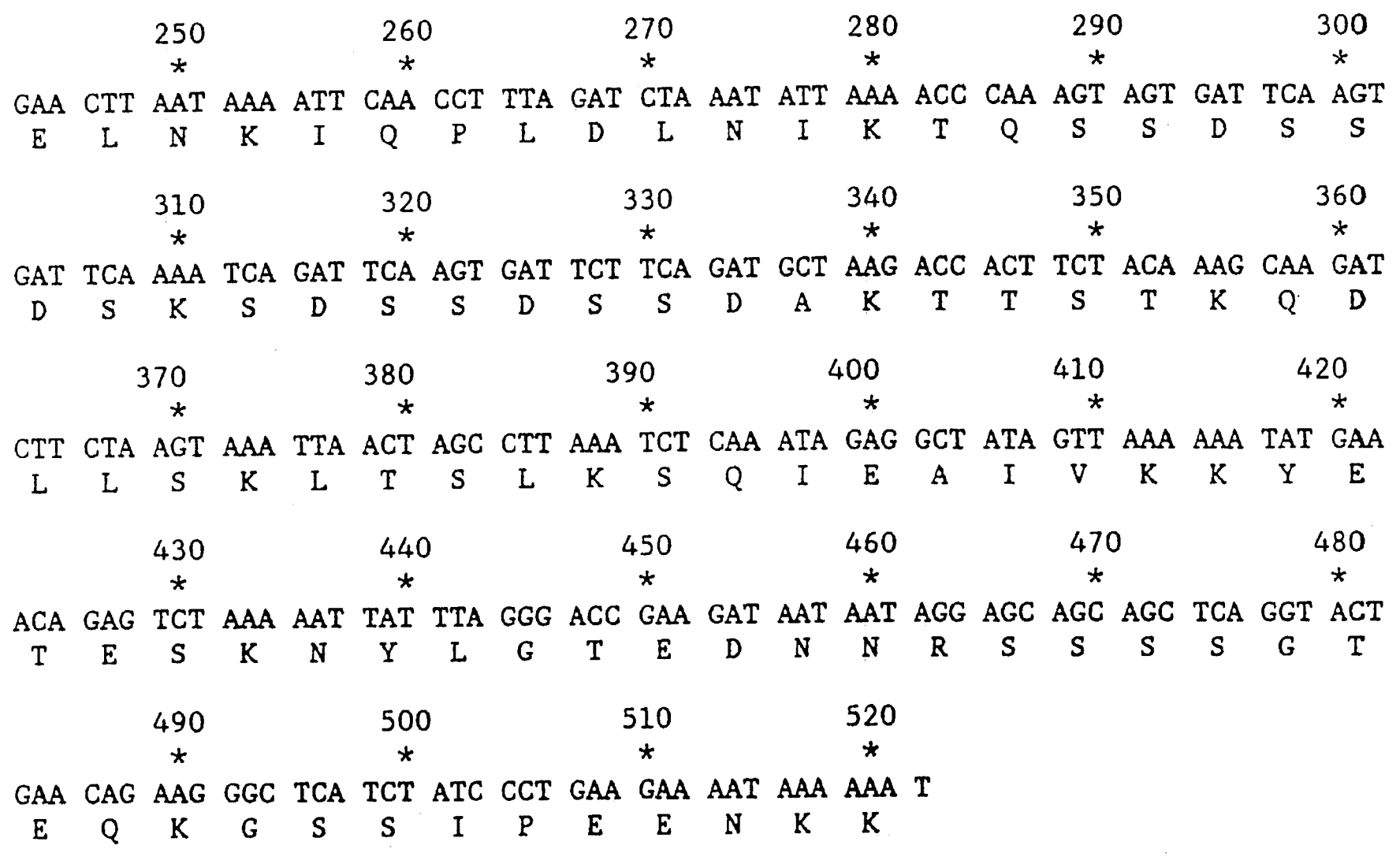

```
         250        260        270        280        290        300
          *          *          *          *          *          *
GAA CTT AAT AAA ATT CAA CCT TTA GAT CTA AAT ATT AAA ACC CAA AGT AGT GAT TCA AGT
 E   L   N   K   I   Q   P   L   D   L   N   I   K   T   Q   S   S   D   S   S 310        320        330        340        350        360
          *          *          *          *          *          *
GAT TCA AAA TCA GAT TCA AGT GAT TCT CAA AAG ACC ACT TCT ACA AAG CAA GAT
 D   S   K   S   D   S   S   D   S   Q   K   T   T   S   T   K   Q   D 370        380        390        400        410        420
          *          *          *          *          *          *
CTT CTA AGT AAA TTA ACT AGC CTT AAA TCT CAA ATA GAG GCT ATA GTT AAA TAT GAA
 L   L   S   K   L   T   S   L   K   S   Q   I   E   A   I   V   K   Y   E 430        440        450        460        470        480
          *          *          *          *          *          *
TCT AAA AAT TAT TTA GGG ACC GAA GAT AAT AGG AGC AGC TCA GGT ACT
 S   K   N   Y   L   G   T   E   D   N   N   R   S   S   S   G   T 490        500        510        520
          *          *          *          *
GAA CAG AAG GGC TCA TCT ATC CCT GAA GAA AAT AAA AAA T
 E   Q   K   G   S   S   I   P   E   E   N   K   K
```

FIG. 2A

```
  1 GGTACCCGGG GATCTTAATA AATTTATCTC TTTTATACA GCCGTAAATT CAAAAATTCA
 61 AAAATTTTGA GGTCTAGTTT TGCCCCAAAT AAACCTTTTT TTGAGTTTAT TAATTTAATT
121 CCTGATGATA AAAATCAAAC ATTTACCCTT CAATTTCGGG CCAAAACACC AATTAGATAA
181 TAATTATACC GCATATTCAT CAATTTTAAG TAAAAAAATT GCTTATGCTC AACGTTCCCA
241 GTTTGCCTTA GCTGATTTTA ATGCAATCAT AGTAAAATCA CCAAAGTTCA ACAAAATTTC
301 CAAAATCTTC GGGAAACTGA TTTTTCAnTC GACTTTTCTT CAAGTCAAAC CTCATTAGCA
361 TCACAAAAAA TTCCTTTCT TACCCGCGTT GAAGATTTTG CCGCAGATAT TAACAAATCC
421 GGAAACCAAG AAGAGGCAAT TTCAAGAATT TCGAAATATT TCCCTGATTT TCAAAGATAT
481 ATTCATGAGT TAAAAGATGA TCCAAATAAT GTTTTACCTT TTAAAAAGGT AAATTTTGAC
541 TTTAGTATTA CAGACGTGCT GGTACCAATG ATTTATTAGT CTAGTGCTAT CTGAACCAAA
601 GTTTTTTAAT AAAAGCAAGA CTCACAAATG AGGCTAAATT TGAACTTCGT GGCCTTAATA
661 TTGAAGAAGC AGAAATGCTG GAAGAGATTA AATTAGCTTC CAGTTGATCA ATTTGTTGTT
721 AACCTTGAAA CCGATCTAAA ACCAGGTCAA GCCCCAGAAA AGTCACAAAA ACCTCAAAGT
781 GAACAAACCG AGATTAAAAA AACTTATTTG CCGAATTAGT AAATTTAAGC AAAATAACCA
841 TGCGCAAAGT TCAGCTTAGC GACTTTAAGG TAGCTCCACA GACAAGTCT TCGCAACCAA
901 AGCAAGTTAA AGCAAGTGTG TCAGCTTGAT CCAATTTAGA TCAAGGGCAA GAAAAATAGA
```

FIG. 2B

```
 961 ATTTTAGTTC GGGTTAGTCA GCAAAGTTCG AATCCACAAC AACAACAACA ACAACCTCAA
1021 CCTCAGAGTC AGCCCCAACC TCAACCTCAG AGTCAACCTC AATCTCAGCC GCAGCCTAAT
1081 GCTCAAACTC AGCCTAAAGC TCAAATTCAA AGCTCTCCTA AGCTCCAGT CCAAAAACCG
1141 GCAACTCCTG ATCCATCTAA ATCATTAAAA TTAGAACAAA ACGTGCCAGA GACTTTCTTA
1201 AAGAGTTTAA TAAAACATTT TAGAGGTCTA ATAAACTTAA ATCACAAAAA CTAGAAGAAA
1261 AAATTAATTC TGAATATTTA TCTAATAAAA TTGGAATTGA TCTTGGCGGT TCTAAAGAAA
1321 TACATTAGTA ATAATCAAGG GATTGAATAT ACTTTTGATA TTCCAAATGC AAAAATAAGG
1381 GATGCTCAAG ATGGAATTAG AAGCCATATT GAAATTCCAG TAACAATTAG TCTTTGATCA
1441 AGTTTCTTTG GTGATTCAGA TAATGTTTTA CTAAAATCAA AAACAGAAAC TTTACTACTC
1501 CCTTATTTCC AAAAGGAAAC TACATCTGAG TCAAAAGACC AAAAAGTAGG ACATACCCAA
1561 AAAGAACTCG ATCTAAATCA GAAACTAGTT TATCAACTCA GTGAACTACC AGGAACTAGC
1621 ACCCAAGGTT CTTCTGGATC TAGTACACAA ACAGAACAAA TTAAAGAAGT TAAACTCCCA
1681 ACACTAACTG CTTTTATTTC AAAAGAAGAA CTACAAGCTC TAATTGATGG GGATAAGAAT
1741 TTAGCTAGTC AGCCAACAAG TCAAGCAGTA TCTGTTTCTC AAGTTAAAGC AACGGAGTTC

▼ Start Protein C gene
1801 CAACAGCAAG AGGCAAATTC AACTAATTCT AGTCCAACTA GTCCAAGCCC TAGTCCAACT
1861 AGTCCAAGTC CAGCTAGTCC AAGTTCAAGT CCTAGTCCAA CTAGTCCTAA AAATCTCGAT
```

FIG. 2C

```
1921 GAAAATATAG GAGTGCCAAA TCCTAGATTT GAGGAAATTA AAAAAATAAT TAGTTCCGAG
1981 TTTACTTATA AGTATAATTT TCGTGCTAAC GAGGCACTTT TAGATGCTTG AGTTGGAAAA
2041 CAAAATTTCC CAAGTCTAAA AGATATTTCC CAGTTTAGAT CAGATCAAAG ATTAGCGAAA
2101 GATTATAAAC TTGTTAACTT AAAATCTAAT AAATTCCTAA AAGAAGATTA TGATGTTCTT
2161 GCTTTTTATG CTAATTTAGT CCAGAAAGAT CCAAGAGAAG TTCTTCAATA TTTATTTGAA
2221 ATTGCAAAAG CTAATAATTT AATTGGTCCT GAAGAAAAAT TAGATCTTAA TCAGATCGAA
2281 GACGATGGCA TCTTTAGACG AGCTAAGGCA ATTAAACTTA TAGATAAATC AAACAATAAC
2341 CAAGGAATTT ATGGATTTTC CTTTAATAAC CAGTTTTTAA AATTCCACGA ACGTGGATGG
2401 ATGTCAACTT TATATTACC TAATGAGGCA AAAACTAAAT TAGCAGATTA TCAAAATCTT
2461 TTATCCGCTG GGATAAGCGA TACCAAGATT TTTAGTGAAC TTAATAAAAT TCAACCTTTA
2521 GATCTAAATA TTAAAACCCA AAGTAGTGAT TCAAGTGATT CAAAATCAGA TTCAAGTGAT
2581 TCTTCAGATG CTAAGACCAC TTCTACAAAG CAAGATCTTC TAAGTAAATT AACTAGCCTT
2641 AAATCTCAAA TAGAGGCTAT AGTTAAAAAA TATGAAACAG AGTCTAAAAA TTATTAGG
2701 ACCGAAGATA ATAATAGGAG CAGCAGCTCA GGTACTGAAC AGAAGGGCTC ATCTATCCCT
2761 GAAGAAAATA AAAAATTCAT CTTGGAAAAT ACAGCAAAAC TTGATAATTT AGCCGATCTA
2821 CTTTTAGCTT TCTATTATCA GGCTAAAAGA TTAAATTTG CAAGTTGAAG TCAACTCCAA
2881 GACGAAGATC TTGACTATCA AATACAATTT GAGAAAGAGG CTAATAACAC TGAGTCTTCA
2941 TCCTCTTCAT CTTCTTCATC CTCTTCATCT TCTTCTGAAA CCGATACAAA CAAACCTGAG
```

FIG. 2D

```
3001 AATGCAGTTG AATATAAACT AACTTATTAT TATAAAATTT ATAATAAAAC TACTAAGAAA
3061 GTAGTTTATA CTACCCCTAA AACAATTATC AAGCTTTATC TTGCAAGTTC TAATATCGGA
3121 GTAAAGAAA  AACAAGAACG TGAATTAAATG TTTTATCTAT CCCATCAGCT
3181 TATTCAATTT TCTATCTAAA ACAAAATGAA TGAGATCAAG TTAAAACAAC AAATAATGGC
3241 CAACAAATGG GTCAGACTGG TTCGAGTCAA GGGTTTGAGT CTCTTGAACC ATTTAAGAAA
3301 ATCCAAGAGA TAGTCCATAA AAATAATAAA GACTATGATC TCAAAGTTGT AACTATCCGC
3361 GATGATGCTT ATGCAGAAAA TGCTAAAATT GTTCACTTAA GGGTGGTTAG AAAAGAAGAA
3421 CAGCAAGCAG AACAAAAAGA GAAAGAGAAG GAAAAAGAAA AGGAAAAGGA ACAAAAAGAA
3481 ACAAGTTCCC AAGGCCAAGT TCCCCAGTCA GCATTTTTCT TCCAAGTTAG ACTTATAAAA
3541 GATGATTATC AAGGAGCAGA GGCCTCAAAT CAGCAAACAA GTAAGCAAGA GATGCAAATG
3601 CCAAACATGG AAAGCCAAAA TTCAGGATCT TCTTCTAGTG CTCCTGCAGC AGCTGCTGCT
3661 AAAGCGGCGA AGTAAAAATA TTATATCTTC GAAAGGATAA GTAATGAACC AATTTGACGA
         ▼ End Protein C gene
3721 AAAAGAGAAA CAACATAATA AAGCAAAAGC AATTCTTTCA ACCGGGTTTT CGGTTACATC
3781 AATTGCAACT ACAGTTGTAG CAGTCCCAAT TGGACTAACA CAAAGTGTG ATTTTTGAGA AATCATTTAG
3841 TTCCCAAGTT TCAGGAGGAG TCGATAAGAA CAAAGTGTG GATTTAAAAT CAGATTCAGA
3901 TCAAATCTTC TCAGAAGAAG ATTTTATAGG AGCAGTTGAG AATCTTAAAC TTTTTGATAA
3961 ATATAAACAT CTAACAGCAA GAATGGCATT AGGTCTTGCC AGGGAAGCAG CTAATGCCAT
```

FIG. 2E

```
4021 AACTTTTACA TCTTATGACA ACACCCCAAT TTACAAAGCA TTTCATTTTA CGATTTCTTT
4081 TGGATATTTC CGATGCCTTT GCGGCTAATA AGAAGTAAA AGCGGTAGTA GTTAGTGCAT
4141 ATTCCCAAAA AGTATCAAGT TACCTATTCA AGACTAACTT CTCTAAAAGG GTTGAAAAGA
4201 AGAAGATGAT GATTTTGGCG ATGATATTAT AGATTATCAA ATTAATCAAG AGCTTTCAGG
4261 TCTATCACTT TCTTCCCTAG CCCCTGAAAG GTGCGCCATCT TTTAGCCTCA GAAATGGCTT
4321 TTCGGCTTGA TAATGACTTT CAAGCGGGCAT ATAAAAAAAC AGGATCAAGA GCCGAGCTTT
4381 TCGCCAGGCC TTGATAAAA ATTATCTTGG TTATAACTTA GTTAACCGCC AAGGTTTGCC
4441 CACTATGCTC CAAAAGGGTT ATGTGCTAGC CCCCAAAACA ATTGAAAATA AAAATGCAAG
4501 CGAAGAAAAA TTTAGTAAAT ATAAATGAAA ATGACCCGTG CAAGGGG....(approxi-
     mately 1700 base pairs unsequenced DNA).
```

FIG. 3

| AMINO ACID SEQUENCE | POSITION IN PROTEIN C FROM AA# | TO AA# |
|---|---|---|
| QQQEANSTNSSP(amino terminus) | 1 | 12 |
| IGVPNPRFE | 43 | 51 |
| NFRANEAL | 66 | 73 |
| VGKQNFPSLKDISQF | 78 | 92 |
| KFLKEDYDVLAFYANLVQKDPREVLQYLFEIAK ANNLIGPEEKLDL | 111 | 156 |
| HER | 196 | 198 |
| LADYQNL | 214 | 220 |
| TTSTKQDLLSKLTSL | 266 | 280 |
| NYLGTEDNNRSSSSGTEQK | 297 | 315 |
| DEDLDYQIQFE | 361 | 373 |
| TIIKLY | 428 | 433 |
| LSIPSAY | 455 | 461 |
| YLKQNEWD | 465 | 472 |

FIG. 4A

```
      10          20          30          40          50          60
       *           *           *           *           *           *
CAA CAG GAA GCA AAT TCA ACT AAT TCT AGT CCA ACT AGT CCA AGC CCT AGT CCA ACT
 Q   Q   E   A   N   S   T   N   S   S   P   T   S   P   S   P   S   P   T 70          80          90         100         110         120
       *           *           *           *           *           *
AGT CCA AGT CCA GCT AGT CCA AGT TCA AGT CCT AGT CCA ACT CCT AAA AAT CTC GAT
 S   P   S   P   A   S   P   S   S   S   P   S   P   T   P   K   N   L   D 130         140         150         160         170         180
       *           *           *           *           *           *
GAA AAT ATA GGA GTG CCA AAT CCT AGA TTT GAG GAA ATT AAA AAA ATA ATT AGT CCC GAG
 E   N   I   G   V   P   N   P   R   F   E   E   I   K   K   I   I   S   E 190         200         210         220         230         240
       *           *           *           *           *           *
TTT ACT TAT AAG TAT AAT TTT CGT GCT AAC GAG GCA CTT GAT GCT TGA GTT GGA AAA
 F   T   Y   K   Y   N   F   R   A   N   E   A   L   D   A   W   V   G   K 250         260         270         280         290         300
       *           *           *           *           *           *
CAA AAT TTC CCA AGT CTA AAA GAT ATT TCC CAG TTT AGA TCA GAT CAA AGA TTA GCG AAA
 Q   N   F   P   S   L   K   D   I   S   Q   F   R   S   D   Q   R   L   A   K
```

FIG. 4B

```
        310         320         330         340         350         360
         *           *           *           *           *           *
GAT TAT AAA CTT GTT AAC TTA AAA TCT AAT AAA GAA GAT TAT GAT GTT CTT
 D   Y   K   L   V   N   L   K   S   N   K   E   D   Y   D   V   L 370         380         390         400         410         420
         *           *           *           *           *           *
GCT TTT TAT GCT AAT TTA GTC CAG AAA GAT CCA AGA GAA GTT CTT CAA TAT TTA GAA
 A   F   Y   A   N   L   V   Q   K   D   P   R   E   V   L   Q   Y   L   E 430         440         450         460         470         480
         *           *           *         ▼ Start R69    *           *
ATT GCA AAA GCT AAT AAT TTA ATT GGT CCT GAA GAA AAA CTT GAT AAA ATC GAA
 I   A   K   A   N   N   L   I   G   P   E   E   K   L   D   K   I   E 490         500         510         520         530         540
         *           *           *           *           *           *
GAC GAT GGC ATC TTT AGA CGA GCT AAG GCA ATT AAA CTT ATA GAT AAA TCA AAC AAT AAC
 D   D   G   I   F   R   R   A   K   A   I   K   L   I   D   K   S   N   N   N 550         560         570         580         590         600
         *           *           *           *           *           *
CAA GGA ATT TAT GGA TTT TCC TTT AAT AAC CAG TTT TTA AAA TTC CAC GAA CGT GGA TGG
 Q   G   I   Y   G   F   S   F   N   N   Q   F   L   K   F   H   E   R   G   W
```

FIG. 4C

```
        610         620         630         640         650         660
         *           *           *           *           *           *
ATG TCA ACT TTA TAT TTA CCT AAT GAG GCA AAA ACT AAA TTA GCA GAT TAT CAA AAT CTT
 M   S   T   L   Y   L   P   N   E   A   K   T   K   L   A   D   Y   Q   N   L 670         680         690         700         710         720
         *           *           *           *           *           *
TTA TCC GCT GGG ATA AGC GAT ACC AAG AGG ATT TTT AGT GAA CTT AAT AAA ATT CAA CCT TTA
 L   S   A   G   I   S   D   T   K   R   I   F   S   E   L   N   K   I   Q   P   L 730         740         750         760         770         780
         *           *           *           *           *           *
GAT CTA AAT ATT AAA ACC CAA AGT AGT GAT TCA AGT GAT TCA AAA TCA CTA AGT GAT
 D   L   N   I   K   T   Q   S   S   D   S   S   D   S   K   S   L   S   D 790         800         810         820         830         840
         *           *           *           *           *           *
TCT TCA GAT GCT AAG ACC ACT TCT ACA AAG CAA GAT CTT CTA AGT AAA TTA ACT AGC CTT
 S   S   D   A   K   T   T   S   T   K   Q   D   L   L   S   K   L   T   S   L 850         860         870         880         890         900-
         *           *           *           *           *           *
AAA TCT CAA ATA GAG GCT ATA GTT AAA AAA TAT GAA ACA GAG TCT AAA AAT TAT TTA GGG
 K   S   Q   I   E   A   I   V   K   K   Y   E   T   E   S   K   N   Y   L   G
```

FIG. 4D

```
     910            920            930            940            950            960
      *              *              *              *              *              *
ACC GAA GAT AAT AAT AGG AGC AGC TCA GGT ACT GAA CAG AAG GGC TCA TCT ATC CCT
 T   E   D   N   N   R   S   S   S   G   T   E   Q   K   G   S   S   I   P 970            980            990           1000           1010           1020
      *              *              *              *              *              *
   End R69 ▼
GAA GAA AAT AAA AAA TTC ATC TTG GAA AAT ACA GCA AAA CTT GAT AAT TTA GCC GAT CTA
 E   E   N   K   K   F   I   L   E   N   T   A   K   L   D   N   L   A   D   L 1030           1040           1050           1060           1070           1080
      *              *              *              *              *              *
CTT TTA GCT TTC TAT TAT CAG GCT AAA AGA TTA AAT TTT GCA AGT TGA AGT CAA CTC CAA
 L   L   A   F   Y   Y   Q   A   K   R   L   N   F   A   S   W   S   Q   L   Q 1090           1100           1110           1120           1130           1140
      *              *              *              *              *              *
GAC GAA GAT CTT GAC TAT CAA ATA CAA TTT GAG AAA GAG AAA GCT AAT AAC ACT GAG TCT TCA
 D   E   D   L   D   Y   Q   I   Q   F   E   K   E   K   A   N   N   T   E   S   S
```

FIG. 4E

```
      1150      1160      1170      1180      1190      1200
       *         *         *         *         *         *
TCC TCT TCA TCT TCT TCA TCC TCT TCA TCT TCT TCT GAA ACC GAT ACA AAC AAA CCT GAG
 S   S   S   S   S   S   S   S   S   S   S   S   E   T   D   T   N   K   P   E
      1210      1220      1230      1240      1250      1260
       *         *         *         *         *         *
AAT GCA GTT GAA TAT AAA CTA ACT TAT TAT TAT AAA ATT TAT AAT AAA ACT ACT AAG AAA
 N   A   V   E   Y   K   L   T   Y   Y   Y   K   I   Y   N   K   T   T   K   K
```

FIG. 4F

```
      1270        1280        1290        1300        1310        1320
        *           *           *           *           *           *
GTA GTT TAT ACT ACC CCT AAA ACA ATT ATC AAG CTT TAT CTT GCA AGT TCT AAT ATC GGA
 V   V   Y   T   T   P   K   T   I   I   K   L   Y   L   A   S   S   N   I   G 1330        1340        1350        1360        1370        1380
        *           *           *           *           *           *
GTT AAA GAA AAA CAA GAA CGT GAA TTA ATG AAT AAA TTA GTT TTA TCT ATC CCA TCA GCT
 V   K   E   K   Q   E   R   E   L   M   N   K   L   V   L   S   I   P   S   A 1390        1400        1410        1420        1430        1440
        *           *           *           *           *           *
TAT TCA ATT TTC TAT CTA AAA CAA AAT GAA TGA GAT CAA GTT AAA ACA ACA AAT AAT GGC
 Y   S   I   F   Y   L   K   Q   N   E   W   D   Q   V   K   T   T   N   N   G 1450        1460        1470        1480        1490        1500
        *           *           *           *           *           *
CAA ATG GGT CAG ACT GGT TCG AGT CAA GGG TTT GAG TCT CTT GAA CCA TTT AAG AAA
 Q   M   G   Q   T   G   S   S   Q   G   F   E   S   L   E   P   F   K   K 1510        1520        1530        1540        1550        1560-
        *           *           *           *           *           *
CAA CAA ATG AAA AAT AAT AAA GAC TAT GAT CTC AAA GTT ACT ATC CGC
 Q   Q   M   K   N   N   K   D   Y   D   L   K   V   T   I   R

ATC CAA GAG ATA GTC CAT
 I   Q   E   I   V   H
```

FIG. 4G

```
                1570          1580          1590           1600          1610          1620
                  *             *             *              *             *             *
GAT GAT GCT TAT GCA GAA AAT GCT AAA ATT GTT CAC TTA AGG GTG GTT AGA AAA GAA GAA
 D   D   A   Y   A   E   N   A   K   I   V   H   L   R   V   V   R   K   E   E 1630          1640          1650           1660          1670          1680
                  *             *             *              *             *             *
CAG CAA GCA GAA CAA AAA GAG AAA GAG AAG GAA AAA GAA AAG GAA AAG GAA CAA AAA GAA
 Q   Q   A   E   Q   K   E   K   E   K   E   K   E   K   E   K   E   Q   K   E 1690          1700          1710           1720          1730          1740
                  *             *             *              *             *             *
ACA AGT TCC CAA GGC CAA GTT CCC CAG TCA GCA TTT TTC TTC CAA GTT AGA CTT ATA AAA
 T   S   S   Q   G   Q   V   P   Q   S   A   F   F   F   Q   V   R   L   I   K
```

FIG. 4H

```
              1750        1760        1770        1780        1790        1800
               *           *           *           *           *           *
GAT GAT TAT CAA GGA GCA GAG GCC TCA AAT CAG CAA ACA AGT AAG CAA GAG ATG CAA ATG
 D   D   Y   Q   G   A   E   A   S   N   Q   Q   T   S   K   Q   E   M   Q   M 1810        1820        1830        1840        1850        1860
               *           *           *           *           *           *
CCA AAC ATG GAA AGC CAA AAT TCA GGA TCT TCT TCT AGT GCT CCT GCA GCA GCT GCT GCT
 P   N   M   E   S   Q   N   S   G   S   S   S   S   A   P   A   A   A   A   A

1870
               *
AAA GCG GCG AAG TAA
 K   A   A   K   -
```

FIG. 5A

```
                    Bam HI                    TC3 coupler
                    GGATCCGATCTTGGAGGATGATTAAATG
                                                   Met N-Terminus of Protein C
                                                                        Eco RI
DNA modified         caG cag caG gaA gca aaC tcC ac  aat tct
DNA original         caa cag caa gag gca aat tca act aat tct
Amino Acid Sequence  Gln Gln Gln Glu Ala Asn Ser Thr Asn Ser agC ccG act agC   cc  ccG agc ccG act
                     agt cca cct agt   ca  cca agc cct act
                     Ser Pro Thr Ser Pro Pro Ser Pro Ser Pro Thr
                     Spe I                                    Spe I
```

FIG. 5B

```
        Ser  Pro  Ser  Pro  Ala  Ser  Pro  Ser  Ser
        agC  ccG  agc  ccG  gct  agc  ccG  agc  tcc  agc
        agt  cca  agt  cca  gct  agt  cca  agt  tca  agt
                            [Nhe I]

Pro  Ser  Pro  Thr  Ser  Pro  . . .
        ccG  agC  ccG  act  agt  ccG              cct
        cct  agt  cca  act  agt  cca              cct
                       [Spe I]
```

FIG. 6A

```
                                                    -20              -10
                                                     *                *
                                        GAT CCG ATC TTG GAG GAT GAT TAA
                                         D   P   I   L   E   D   D   *

10                  20                  30                  40                  50                  60
  *                   *                   *                   *                   *                   *
ATG CAG CAG GAA GCA AAC TCC ACG AAT TCT AGC CCG ACT AGC CCG AGC CCG
 M   Q   Q   E   A   N   S   T   N   S   S   P   T   S   P   S   P 70                  80                  90                 100                 110                 120
  *                   *                   *                   *                   *                   *
ACT AGC CCG AGC CCG GCT AGC CCG AGC CCG AGC TCC AGC CCG ACT AGT CCT AAA AAT CTC
 T   S   P   S   P   A   S   P   S   P   S   S   S   P   T   S   P   K   N   L 130                 140                 150                 160                 170                 180
  *                   *                   *                   *                   *                   *
GAT GAA AAT ATA GGA GTG CCA AAT CCT AGA TTT GAG GAA ATT AAA AAA ATA ATT AGT TCC
 D   E   N   I   G   V   P   N   P   R   F   E   E   I   K   K   I   I   S   S 190                 200                 210                 220                 230                 240
  *                   *                   *                   *                   *                   *
GAG TTT ACT TAT AAG TAT AAT TTT CGT GCT AAC GAG GCA CTT GAT GCT TGG GTT GGA
 E   F   T   Y   K   Y   N   F   R   A   N   E   A   L   D   A   W   V   G
```

FIG. 6B

```
       250        260        270        280        290        300
        *          *          *          *          *          *
AAA CAA AAT TTC CCA AGT CTA AAA GAT ATT TCC CAG TTT AGA TCA GAT CAA AGA TTA GCG
 K   Q   N   F   P   S   L   K   D   I   S   Q   F   R   S   D   Q   R   L   A 310        320        330        340        350        360
        *          *          *          *          *          *
AAA GAT TAT AAA CTT GTT AAC TTA AAA TCT AAT AAA TTC CTA AAA GAA GAT TAT GAT GTT
 K   D   Y   K   L   V   N   L   K   S   N   K   F   L   K   E   D   Y   D   V 370        380        390        400        410        420
        *          *          *          *          *          *
CTT GCT TTT TAT GCT AAT TTA GTC CAG AAA GAT CCA AGA GAA GTT CTT CAA TAT TTA TTT
 L   A   F   Y   A   N   L   V   Q   K   D   P   R   E   V   L   Q   Y   L   F 430        440        450        460        470        480
        *          *          *          *          *          *
GAA ATT GCA AAA GCT AAT AAT TTA ATT GGT CCT GAA GAA AAA TTA GAT CTT AAT CAG ATC
 E   I   A   K   A   N   N   L   I   G   P   E   E   K   L   D   L   N   Q   I
```

FIG. 6C

```
      490       500       510       520       530       540
       *         *         *         *         *         *
GAA GAC GAT GGC ATC TTT AGA CGA GCT AAG GCA ATT AAA CTT ATA GAT AAA TCA AAC AAT
 E   D   D   G   I   F   R   R   A   K   A   I   K   L   I   D   K   S   N   N 550       560       570       580       590       600
       *         *         *         *         *         *
AAC CAA GGA ATT TAT GGA TTT TCC TTT AAT AAC CAG TTT TTA AAA TTC CAC GAA CGT GGA
 N   Q   G   I   Y   G   F   S   F   N   N   Q   F   L   K   F   H   E   R   G
```

FIG. 6D

```
         610          620          630          640          650          660
          *            *            *            *            *            *
TGG ATG TCA ACT TTA TAT TTA CCT AAT GAG GCA AAA ACT AAA TTA GCA GAT TAT CAA AAT
 W   M   S   T   L   Y   L   P   N   E   A   K   T   K   L   A   D   Y   Q   N 670          680          690          700          710          720
          *            *            *            *            *            *
CTT TTA TCC GCT GGG ATA AGC GAT ACC AAG ATT TTT AGT GAA CTT AAT ATT CAA CCT
 L   L   S   A   G   I   S   D   T   K   I   F   S   E   L   N   I   Q   P 730          740          750          760          770          780
          *            *            *            *            *            *
TTA GAT CTA AAT ATT AAA ACC CAA AGT AGT GAT TCA AGT GAT TCA AAA TCA GAT TCA AGT
 L   D   L   N   I   K   T   Q   S   S   D   S   S   D   S   K   S   D   S   S 790          800          810          820          830          840
          *            *            *            *            *            *
GAT TCT GAT GCT AAG ACC ACT TCT ACA AAG CAA GAT CTT CTA AGT AAA TTA ACT AGC
 D   S   D   A   K   T   T   S   T   K   Q   D   L   L   S   K   L   T   S 850          860          870          880          890          900
          *            *            *            *            *            *
CTT AAA TCT CAA ATA GAG GCT ATA GTT AAA AAA TAT GAA ACA GAG TCT AAA AAT TAT TTA
 L   K   S   Q   I   E   A   I   V   K   K   Y   E   T   E   S   K   N   Y   L
```

FIG. 6E

```
GGG ACC GAA GAT AAT AAT AGG AGC AGC TCA GGT ACT GAA CAG AAG GGC TCA TCT ATC
 G   T   E   D   N   N   R   S   S   S   G   T   E   Q   K   G   S   S   I
910         920         930         940         950         960
 *           *           *           *           *           *

CCT GAA GAA AAT AAA AAA TTC ATC TTG GAA AAT ACA GCA AAA CTT GAT AAT TTA GCC GAT
 P   E   E   N   K   K   F   I   L   E   N   T   A   K   L   D   N   L   A   D
970         980         990         1000        1010        1020
 *           *           *           *           *           *

CTA CTT TTA GCT TTC TAT TAT CAG GCT AAA AGA TTA AAT TTT GCA AGT TGG AGT CAA CTC
 L   L   L   A   F   Y   Y   Q   A   K   R   L   N   F   A   S   W   S   Q   L
1030        1040        1050        1060        1070        1080
 *           *           *           *           *           *

CAA GAC GAA GAT CTT GAC TAT CAA ATA CAA TTT GAG AAA GAG GCT AAT AAC ACT GAG TCT
 Q   D   E   D   L   D   Y   Q   I   Q   F   E   K   E   A   N   N   T   E   S
1090        1100        1110        1120        1130        1140
 *           *           *           *           *           *
```

```
            1150        1160        1170        1180        1190        1200
             *           *           *           *           *           *
TCA TCC TCT TCA TCT TCA TCC TCT TCA TCT TCT TCT GAA ACC GAT ACA AAC AAA CCT
 S   S   S   S   S   S   S   S   S   S   S   S   E   T   D   T   N   K   P 1210        1220        1230        1240        1250        1260
             *           *           *           *           *           *
GAG AAT GCA GTT GAA TAT AAA CTA ACT TAT AAA ATT TAT AAT AAA ACT ACT AAG
 E   N   A   V   E   Y   K   L   T   Y   K   I   Y   N   K   T   T   K
```

FIG. 6F

FIG. 6G

```
         1270        1280        1290        1300        1310        1320
          *           *           *           *           *           *
AAA GTA GTT TAT ACT ACC CCT AAA ACA ATT ATC AAG CTT TAT CTT GCA AGT TCT AAT ATC
 K   V   V   Y   T   T   P   K   T   I   I   K   L   Y   L   A   S   S   N   I 1330        1340        1350        1360        1370        1380
          *           *           *           *           *           *
GGA GTT AAA GAA AAA CAA GAA CGT GAA TTA ATG AAT AAA TTA GTT TTA TCT ATC CCA TCA
 G   V   K   E   K   Q   E   R   E   L   M   N   K   L   V   L   S   I   P   S 1390        1400        1410        1420        1430        1440
          *           *           *           *           *           *
GCT TAT TCA ATT TTC TAT CTA AAA CAA AAT GAA TGG GAT CAA GTT AAA ACA ACA AAT AAT
 A   Y   S   I   F   Y   L   K   Q   N   E   W   D   Q   V   K   T   T   N   N 1450        1460        1470        1480        1490        1500
          *           *           *           *           *           *
CAA CAA ATG GGT CAG ACT GGT TCG AGT CAA GGG TTT GAG TCT CTT GAA CCA TTT AAG
 Q   Q   M   G   Q   T   G   S   S   Q   G   F   E   S   L   E   P   F   K 1510        1520        1530        1540        1550        1560
          *           *           *           *           *           *
GGC CAA CAA GAG ATA GTC CAT AAA AAT AAT AAA GAC TAT GAT CTC AAA GTT GTA ACT ATC
 G   Q   Q   E   I   V   H   K   N   N   K   D   Y   D   L   K   V   V   T   I

AAA ATC CAA GAG ATA GTC CAT AAA AAT AAT AAA GAC TAT GAT CTC AAA GTT GTA ACT ATC
 K   I   Q   E   I   V   H   K   N   N   K   D   Y   D   L   K   V   V   T   I
```

FIG. 6H

```
       1570        1580        1590        1600        1610        1620
        *           *           *           *           *           *
CGC GAT GAT GCT TAT GCA GAA AAT GCT AAA ATT GTT CAC TTA AGG GTG GTT AGA AAA GAA
 R   D   D   A   Y   A   E   N   A   K   I   V   H   L   R   V   V   R   K   E 1630        1640        1650        1660        1670        1680
        *           *           *           *           *           *
GAA CAG CAA GCA GAA CAA AAA GAG AAG GAA AAA GAA AAG GAA AAG GAA CAA AAA
 E   Q   Q   A   E   Q   K   E   K   E   K   E   K   E   K   E   Q   K 1690        1700        1710        1720        1730        1740
        *           *           *           *           *           *
GAA ACA AGT TCC CAA GGC CAA GTT CCC CAG TCA GCA TTT TTC TTC CAA GTT AGA CTT ATA
 E   T   S   S   Q   G   Q   V   P   Q   S   A   F   F   F   Q   V   R   L   I 1750        1760        1770        1780        1790        1800
        *           *           *           *           *           *
AAA GAT GAT TAT CAA GGA GCA GAG GCC TCA AAT CAG CAA ACA AGT AAG CAA GAG ATG CAA
 K   D   D   Y   Q   G   A   E   A   S   N   Q   Q   T   S   K   Q   E   M   Q
```

FIG. 61

```
         1810        1820        1830        1840        1850        1860
          *           *           *           *           *           *
ATG CCA AAC ATG GAA AGC CAA AAT TCA GGA TCT TCT TCT AGT GCT CCT GCA GCT GCT
 M   P   N   M   E   S   Q   N   S   G   S   S   S   S   A   P   A   A   A 1870        1880        1890        1900        1910        1920
          *           *           *           *           *           *
GCT AAA GCG GCG AAG TAA AAA TAT TAT ATC TTC GAA AGG ATA AGT AAT GAA CCA ATT TGA
 A   K   A   A   K   -

1930        1940        1950        1960        1970        1980
          *           *           *           *           *           *
CGA AAA AGA GAA ACA ACA TAA TAA AGC AAA AGC AAT TCT TTC AAC CGG GTT TTC GGT TAC
```

FIG. 6J

```
         1990      2000      2010      2020      2030      2040
          *         *         *         *         *         *
ATC AAT TGC AAC TAC AGT TGT AGC AGT CCC AAT TGG ACT AAC AAT TTT TGA GAA ATC ATT
         2050      2060      2070      2080      2090      2100
          *         *         *         *         *         *
TAG TTC CCA AGT TTC AGG AGG AGT CGA TAA GAA CAA AGT TGT GGA TTT AAA ATC AGA TTC
         2110      2120      2130      2140      2150      2160
          *         *         *         *         *         *
AGA TCA AAT CTT CTC AGA AGA AGA TTT TAT AGG AGC AGT TGA GAA TCT TAA ACT TTT TGA
         2170      2180      2190      2200      2210      2220
          *         *         *         *         *         *
TAA ATA TAA ACA TCT AAC AGC AAG AAT GGC ATT AGG TCT TGC CAG GGA AGC AGC TAA TGC
         2230      2240      2250      2260      2270      2280
          *         *         *         *         *         *
CAT AAC TTT TAC ATC TTA TGA CAA CAC CCC AAT TTA CAA AGC ATT TCA TTT TAC GAT TTC
         2290      2300      2310      2320      2330      2340
          *         *         *         *         *         *
TTT TGG ATA TTT CCG ATG CCT TTG CGG CTA ATA AAG AAG TAA AAG CGG TAG TAG TTA GTG
```

FIG. 6K

```
         2350           2360           2370           2380           2390           2400
          *              *              *              *              *              *
CAT ATT CCC AAA AAG TAT CAA GTT ACC TAT TCA AGA CTA ACT TCT CTA AAA GGG TTG AAA
         2410           2420           2430           2440           2450           2460
          *              *              *              *              *              *
AGA AGA AGA TGA TTT TGG CGA TGA TAT TAT AGA TTA TCA AAT TAA TCA AGA GCT TTC
         2470           2480           2490           2500           2510           2520
          *              *              *              *              *              *
AGG TCT ATC ACT TTC CCT AGC CCC TGA AAG GTG CGC ATC TTT TAG CCT CAG AAA TGG
         2530           2540           2550           2560           2570           2580
          *              *              *              *              *              *
CTT TTC GGC TTG ATA ATG ACT TTC AAG CGG CAT ATA AAA CAG GAT CAA GAG CCG AGC
         2590           2600           2610           2620           2630           2640
          *              *              *              *              *              *
TTT TCG CCA GGC CTT GAT AAA AAA TTA TCT TGG TTA TAA CTT AGT TAA CCG CCA AGG TTT
```

FIG. 6L

```
         2650        2660        2670        2680        2690        2700
          *           *           *           *           *           *
GCC CAC TAT GCT CCA AAA GGG TTA TGT GCT AGC CCC CAA AAC AAT TGA AAA TAA AAA TGC
         2710        2720        2730        2740        2750
          *           *           *           *           *
AAG CGA AGA AAA ATT TAG TAA ATA TAA ATG AAA ATG ACC CGT GCA AGG GG
```

FIG. 7A

```
                                                    -20                 -10
                                                     *                   *
                                         GAT CCG ATC TTG GAG GAT GAT TAA
                                          D   P   I   L   E   D   D   *

10              20              30              40              50              60
   *               *               *               *               *               *
ATG CAG CAG GAA GCA AAC TCC ACG AAT TCT AGC CCG
 M   Q   Q   E   A   N   S   T   N   S   S   P 70              80              90             100             110             120
   *               *               *               *               *               *
ACT AGC CCG GCT AGC CCG AGC CCG ACT AGT CCT AAA AAT CTC
 T   S   P   A   S   P   S   P   T   S   P   K   N   L 130             140             150             160             170             180
   *               *               *               *               *               *
GAT GAA AAT ATA GGA GTG CCA AAT CCT AGA TTT GAG GAA ATT AAA AAA ATA ATT AGT TCC
 D   E   N   I   G   V   P   N   P   R   F   E   E   I   K   K   I   I   S   S 190             200             210             220             230             240
   *               *               *               *               *               *
GAT GAA AAT ATA GGA GTG CCA AAT CCT AGA TTT GAG GAA ATT AAA AAA ATA ATT AGT TCC
GAG TTT ACT TAT AAG TAT AAT TTT CGT GCT AAC GAG GCA CTT TTA GAT GCT [TGG] GTT GGA
 E   F   T   Y   K   Y   N   F   R   A   N   E   A   L   L   D   A  [ W ] V   G
```

FIG. 7B

```
      250         260         270         280         290         300
       *           *           *           *           *           *
AAA CAA AAT TTC CCA AGT CTA AAA GAT ATT TCC CAG TTT AGA TCA GAT CAA AGA TTA GCG
 K   Q   N   F   P   S   L   K   D   I   S   Q   F   R   S   D   Q   R   L   A 310         320         330         340         350         360
       *           *           *           *           *           *
AAA GAT TAT AAA CTT GTT AAC TTA AAA TCT AAT AAA TTC CTA AAA GAA GAT TAT GAT GTT
 K   D   Y   K   L   V   N   L   K   S   N   K   F   L   K   E   D   Y   D   V 370         380         390         400         410         420
       *           *           *           *           *           *
CTT GCT TTT TAT GCT AAT TTA GTC CAG AAA GAT CCA AGA CTT CAA TAT TTA TTT
 L   A   F   Y   A   N   L   V   Q   K   D   P   R   E   V   L   Q   Y   L   F 430         440         450         460         470         480
       *           *           *           *           *           *
GAA ATT GCA AAA GCT AAT AAT TTA ATT GGT CCT GAA GAA AAA TTA GAT CTT AAT CAG ATC
 E   I   A   K   A   N   N   L   I   G   P   E   E   K   L   D   L   N   Q   I
```

FIG. 7C

```
     490       500       510       520       530       540
      *         *         *         *         *         *
GAA GAC GAT GGC ATC TTT AGA CGA GCT AAG GCA ATT AAA CTT ATA GAT AAA TCA AAC AAT
 E   D   D   G   I   F   R   R   A   K   A   I   K   L   I   D   K   S   N   N 550       560       570       580       590       600
      *         *         *         *         *         *
AAC CAA GGA ATT TAT GGA TTT TCC TTT AAT AAC CAG TTT TTA AAA TTC CAC GAA CGT GGA
 N   Q   G   I   Y   G   F   S   F   N   N   Q   F   L   K   F   H   E   R   G
```

FIG. 7D

```
           610                 620                 630                 640                 650                 660
            *                   *                   *                   *                   *                   *
TGG ATG TCA ACT TTA TAT TTA CCT AAT GAG GCA AAA ACT AAA TTA GCA GAT TAT CAA AAT
 W   M   S   T   L   Y   L   P   N   E   A   K   T   K   L   A   D   Y   Q   N 670                 680                 690                 700                 710                 720
            *                   *                   *                   *                   *                   *
CTT TTA TCC GCT GGG ATA AGC GAT ACC AAG ATT TTT AGT GAA CTT AAT AAA ATT CAA CCT
 L   L   S   A   G   I   S   D   T   K   I   F   S   E   L   N   K   I   Q   P 730                 740                 750                 760                 770                 780
            *                   *                   *                   *                   *                   *
TTA GAT CTA AAT ATT AAA ACC CAA AGT GAT TCA AGT GAT TCA AAA TCA GAT TCA AGT AGT
 L   D   L   N   I   K   T   Q   S   D   S   S   D   S   K   S   D   S   S   S 790                 800                 810                 820                 830                 840
            *                   *                   *                   *                   *                   *
GAT TCT TCA GAT GCT AAG ACC ACT TCT ACA AAG CAA GAT CTT CTA AGT AAA TTA ACT AGC
 D   S   S   D   A   K   T   T   S   T   K   Q   D   L   L   S   K   L   T   S
```

FIG. 7E

```
                     850             860             870             880             890             900
                      *               *               *               *               *               *
CTT AAA TCT CAA ATA GAG GCT ATA GTT AAA AAA TAT GAA ACA GAG TCT AAA AAT TAT TTA
 L   K   S   Q   I   E   A   I   V   K   K   Y   E   T   E   S   K   N   Y   L 910             920             930             940             950             960
                      *               *               *               *               *               *
GGG ACC GAA GAT AAT AAT AGG AGC AGC TCA GGT ACT GAA CAG AAG GGC TCA TCT ATC
 G   T   E   D   N   N   R   S   S   S   G   T   E   Q   K   G   S   S   I 970             980             990            1000            1010            1020
                      *               *               *               *               *               *
CCT GAA GAA AAT AAA AAA TTC ATC TTG GAA AAT ACA GCA AAA CTT GAT AAT TTA GCC GAT
 P   E   E   N   K   K   F   I   L   E   N   T   A   K   L   D   N   L   A   D
```

FIG. 7F

```
                1030           1040           1050           1060           1070           1080
                 *              *              *              *              *              *
CTA CTT TTA GCT TTC TAT TAT CAG GCT AAA AGA TTA AAT TTT GCA AGT   TGG   AGT CAA CTC
 L   L   L   A   F   Y   Y   Q   A   K   R   L   N   F   A   S    W    S   Q   L 1090           1100           1110           1120           1130           1140
                 *              *              *              *              *              *
CAA GAC GAA GAT CTT GAC TAT CAA ATA CAA TTT GAG AAA GAG GCT AAT AAC ACT GAG TCT
 Q   D   E   D   L   D   Y   Q   I   Q   F   E   K   E   A   N   N   T   E   S 1150           1160           1170           1180           1190           1200
                 *              *              *              *              *              *
TCA TCC TCT TCA TCT TCT TCA TCC TCT TCA TCT TCT TCT GAA ACC GAT ACA AAC AAA CCT
 S   S   S   S   S   S   S   S   S   S   S   S   S   E   T   D   T   N   K   P 1210           1220           1230           1240           1250           1260
                 *              *              *              *              *              *
GAG AAT GCA GTT GAA TAT AAA CTA ACT TAT TAT TAT AAA ATT TAT AAA ACT ACT AAG
 E   N   A   V   E   Y   K   L   T   Y   Y   Y   K   I   Y   N   K   T   T   K 1270           1280           1290           1300           1310
                 *              *              *              *              *
AAA GTA GTT TAT ACT ACC CCT AAA ACA ATT ATC AAG CTT GGT ACC GAC TAG TAA   -
 K   V   V   Y   T   T   P   K   T   I   I   K   L   G   T   D   -    -   -
```

DNA ENCODING 85KD POLYPEPTIDE USEFUL IN DIAGNOSIS OF MYCOPLASMA INFECTIONS IN ANIMALS

This application is a continuation of application Ser. No. 07/962,075, filed Oct. 16, 1992, now abandoned, which is a continuation of Ser. No. 07/502,640, filed Apr. 2, 1990, now abandoned, which is a continuation in part of Ser. No. 07/196,891, filed May 18, 1988, now abandoned, which is a continuation of Ser. No. 06/889,153, filed Jul. 25, 1986, now abandoned.

BACKGROUND OF THE INVENTION

The present invention relates to a class of polypeptides useful in diagnostic assays to determine the presence of antibodies to Mycoplasma organisms in mammals, particularly in pigs or hogs. The invention also relates to recombinant-DNA methods for the manufacture of these polypeptides and recombinant phage clones containing DNA sequences suitable for use in the recombinant methods. The invention also relates to vaccination compositions and methods of vaccination to inhibit Mycoplasma infections in animals.

Enzootic pneumonia of pigs, also known as virus pneumonia, infectious pneumonia, anterior lobe pneumonia, enzootic virus pneumonia and mycoplasmal pneumonia of swine, rarely causes death, but often results in severe morbidity and reduced performance in weight gain of swine. Originally believed to be caused by a virus, it was determined in 1965 that the causative agent was *Mycoplasma hyopneumoniae,* also known as *Mycoplasma suipneumoniae.*

The disease is transmitted from pig to pig through the nasal passages by airborne organisms expelled from infected pigs. The Mycoplasma establish themselves deep in the apical and cardiac lobes of the lungs where they cause visible plum colored or gray lesions and cause difficulty in breathing and reduced weight gain. The primary infection by *M. hyopneumoniae* may be followed by secondary infection by other mycoplasma species (*M. hyorhinus* and *M. floculare*) as well as bacterial pathogens (Pasterella and Bordetella species).

The Mycoplasmas are prokaryotic cells smaller and simpler in structure than bacteria, but more complex than viruses. Unlike viruses, they are capable of a free living existence, though they are often found in association with eukaryotic cells. They are bounded by a cell membrane but not by a cell wall. They have an extremely small genome, approximately 750,000 base pairs in length.

While this disease is not often fatal, it causes decreased growth and weight gain in the affected animals at a time when the animals are being fed for market. Thus, animals which have been infected with this organism will be worth less at slaughter than will their non-infected counterparts.

Due to the serious economic consequences of pig pneumonia, diagnostic testing methods have been sought which will indicate the presence of an infection caused by *Mycoplasma hyopneumoniae* in swine. The present inventors have discovered a class of polypeptides useful in the diagnosis of this and certain other Mycoplasma infections. These polypeptides, when used in in vitro diagnostic assays, indicate the presence of antibodies against certain Mycoplasma organisms in infected pig and hog sera.

To facilitate use of these polypeptides, the present invention also relates to recombinant-DNA methods for manufacturing the polypeptides. These recombinant-DNA methods utilize DNA sequences contained in various recombinant phage clones which are described herein.

Another object of the present invention is to provide a vaccine composition and a method of vaccination effective for preventing certain Mycoplasma infections in animals.

SUMMARY OF THE INVENTION

It is an object of the present invention to provide polypeptides useful in the diagnosis of certain Mycoplasma infections particularly *Mycoplasma hyopneumoniae* infections in swine. It is also an object of the present invention to identify recombinant-DNA methods for the manufacture of these polypeptides.

Additional objects and advantages of the present invention will be set forth in part in the description which follows, or may be learned from the practice of the invention. The objects and advantages may be realized and attained by means of the instrumentalities and combinations particularly pointed out in the appended claims.

To achieve the objects according to certain preferred embodiments and in accordance with the purposes of the present invention, Proteins A, B, C, D, and E have been disclosed. The DNA corresponding to portions of these proteins is contained on various lambda phages which also are identified herein. Moreover, the entire gene for Protein C has been provided herein.

In addition, a recombinant-DNA method for the manufacture of polypeptides analogous to Mycoplasma surface proteins is disclosed. These proteins are capable of creating an immuno-diagnostic complex when exposed to sera from swine infected with *Mycoplasma hyopneumoniae* and certain other mycoplasma organisms. This method comprises:

(a) Preparation of a DNA sequence coding for a polypeptide possessing antigenic properties analogous to those possessed by a polypeptide produced by Mycoplasma organisms;

(b) Cloning the DNA sequence into a vector capable of being transferred into and replicating in a host organism, such vector containing operations elements for the DNA sequence;

(c) Transferring the vector containing the DNA sequence and operational elements into a host microorganism capable of expressing the antigenic polypeptide;

(d) Culturing the host microorganism under conditions appropriate for amplification of the vector and expression of the polypeptide; and (e) In either order:

(i) harvesting the polypeptides; and (ii) causing the polypeptide to assume a structure whereby it possesses antigenic properties analogous to properties possessed by polypeptides produced by Mycoplasma organisms.

It is understood that the foregoing general description and the following detailed description are exemplary and explanatory only and are not restrictive of the invention as claimed.

BRIEF DESCRIPTION OF THE DRAWING FIGURES

FIG. 1 depicts the entire DNA sequence and translated amino acid sequence of the *Mycoplasma hyopneumoniae* genomic DNA insert in the phage λgtll clone R69. The DNA sequence (upper line) is divided into three base codons which align with the proper reading frame of the gene. The amino acid sequence (lower line) is the translation of the DNA codon directly above, written in the single letter amino acid code as described herein.

FIG. 2 depicts the *Mycoplasma hyopneumoniae* DNA sequence from the recombinant plasmid clone pUC18::28C2 which contains the entire gene for Protein C. A total of 4547 base pairs were sequenced. Approximately 1700 base pairs of DNA downstream were not sequenced. The Protein C gene starts at nucleotide 1801 and ends at nucleotide 3672 of the insert.

FIG. 3 depicts the amino acid sequences of peptides derived from endoproteinase digested purified Protein C and the positions of these sequences in the amino acid sequence of the intact protein. The sequences are written in the single letter amino acid code as described herein.

FIG. 4 depicts the entire DNA sequence and amino acid sequence of the Protein C gene. The DNA sequence (upper line) was directly determined (see Example VIII-B) and the amino acid sequence (lower line) was determined by translation of the DNA sequence above. The underlined segments of the amino acid sequence denote the parts of the sequence for which there is direct amino acid sequencing data (see Example VIII-C and D and FIG. 3). The three UGA codons (TGA in the DNA sequence) are enclosed in boxes. The position of the λgtll clone R69 insert (starting at nucleotide 455 and ending at nucleotide 976) is delineated by marks above the DNA sequence. The amino acid sequence is written in the single letter amino acid code as described herein.

FIG. 5 depicts the modifications made to the 5' end of the Protein C gene for recombinant expression of *E. coli* using the plasmid vector pT5T. The initial 25 bases encode a BamH1 restriction site for connection to the pT5T vector with the TC3 translational coupler ending with the translational stop TAA. Following the TC3 coupler is the restart methionine codon ATG, followed by the Protein C gene. Both the original and modified DNA sequences are shown with the unchanged nucleotides depicted in lower case letters and the modified nucleotides depicted in capital letters in the modified sequence. The translation of these sequences (unchanged between the original and modified sequences) is shown in bold below the DNA sequences. The shaded boxes indicate restriction endonuclease recognition sites in the sequences, with the name of the restriction endonuclease noted above or below the box.

FIG. 6 depicts the DNA sequence and the translated amino acid sequence of the insert in the expression plasmid pT5T::M852 which produces the recombinant full length Protein C. Translation starts at the ATG restart at position 1 which is preceded by the TC3 coupler (See FIG. 5). Translation of the sequence proceeds to the natural stop codon TAA at nucleotide 1876. The three UGA codons (TGA in the DNA sequence) in the Protein C gene have been changed to UGG (TGG) in this clone to permit expression in *E. coli.* These TGG's are denoted by boxes in the sequence. The numbering system is offset by three nucleotides from FIG. 4 because of the addition of the start codon ATG to the 3'-end.

FIG. 7 depicts the DNA sequence and the translated amino acid sequence of the insert in the expression plasmid pT5T::M851 which produces the recombinant truncated Protein C. Translation starts at the ATG restart at position 1 which is preceded by the TC3 coupler (See FIG. 5). Translation of the Protein C sequence proceeds to the HindIII restriction site at nucleotides 1294 to 1299 where the insert is Joined to the pT5T vector which encodes three more amino acids (glycine, threonine and aspartic acid) before a translational stop codon. This insert encompasses only the first two of the three UGA codons in the gene for Protein C (TGA in the DNA sequence) and these have been changed to UGG (TGG) in this clone to permit expression in *E. coli.* These TGG's are denoted by boxes in the sequence. The numbering system is offset by three nucleotides from FIG. 4 because of the addition of the start codon ATG to the 3'-end.

FIG. 8 is a photograph of a Coomassie Blue stained polyacrylamide gel showing the electrophoretically separated proteins in *M. hyopneumoniae extracts S*1, 7S, and 7P (See Example X-A).

FIG. 9 depicts the restriction map of clone pUC18::28C2, the *M. hyopneumoniae* genomic clone containing the entire Protein C gene. The arrows below the main figure depict the sequencing strategy, showing the direction and extent of the sequencing done. Also depicted are the positions of the sequences of clone R69, the original λgtll clone isolated which encodes part of Protein C, and R68, another λgtll clone which starts before the coding region for Protein C and reads into the coding sequence. The positions of the three UGA codons in Protein C coding sequence are also shown.

FIG. 10 depicts certain features of the bacterial expression construct pT5T::M852 which expresses the full length recombinant Protein C. Features are representative only and not drawn to exact scale. The shaded part indicates the *M. hyopneumoniae* segment containing the Protein C gene. Expression construct pT5T::M851, which expresses the truncated Protein C, is essentially the same except that it lacks the ~2 kb HindIII fragment.

DETAILED DESCRIPTION OF THE PREFERRED EMBODIMENTS

Reference will now be made in detail to the presently preferred embodiments of the invention, which, together with the drawings and the following examples, serve to explain the principles of the invention. All references discussed in this specification are hereby incorporated in their entirety by reference. The three letter and one letter designations for amino acids used in this application are as follows:

| AMINO ACID | THREE-LETTER ABBREVIATION | ONE-LETTER SYMBOL |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Termination —
Unknown: *

As noted above, the present invention relates to a class of polypeptides which are useful, inter alia, for in vitro diagnosis of mycoplasma infection in swine. The present invention also relates to vaccine compositions and methods of vaccination including the above-mentioned class of polypeptides. These substantially purified proteins are analogous to various *Mycoplasma hyopneumoniae* proteins which are capable of inducing an immune response when present in swine tissue. Because an immune response has been mounted in infected swine against analogous antigens, the sera of such infected swine will contain antibodies which will recognize one or more of the polypeptides of the present invention. Thus, the instant polypeptides may serve, either in combination or individually, as the active ingredient in an in vitro diagnostic assay to determine the presence in swine sera of antibodies directed toward various Mycoplasma species. Moreover, the instant polypeptides, either in combination or individually, may also be used in vaccine compositions to illicit an immune response in animals to prevent Mycoplasma infections in the vaccinated animals.

As used herein, the term "analogous," when used in connection with a protein, antigen or polypeptide, is intended to mean a polypeptide which is capable of detecting antibodies raised in response to an infection with natural Mycoplasma proteins in swine. A polypeptide possessing analogous antigenic properties will thus exhibit some homology to the native Mycoplasma protein. It should be noted that "analogous" polypeptides, as the term is used herein, may raise an immune response which is stronger than, the same as, or weaker than the response raised by natural Mycoplasma proteins.

By "substantially homologous," as used throughout the ensuing specification and claims, is meant a degree of homology to the protein of interest in excess of that displayed by any previously reported, purified, substantially homologous protein composition. Preferably, the degree of homology is in excess of 60%, and more preferably 75%, with particularly preferred proteins being in excess of 85% or 90% homologous with the native protein. The degree of homology as described above is calculated as the percentage of amino acid residues found in the smaller of the two sequences that align with identical amino acid residues in the sequences being compared when four gaps in a length of 100 amino acids may be introduced to assist in that alignment as set forth by Dayhoff, M. O. in *Atlas of Protein Sequences and Structure,* Vol. 5, page 124 (1972), National Biochemical Research Foundation, Washington, D.C.

As described herein, the protein of the present invention is either isolated from a natural source or is a synthetic polypeptide. The term "synthetic" polypeptide is intended to mean an amino acid sequence which has not previously been isolated from nature in a substantially purified form. In applying this definition, "synthetic" encompasses, among others, polypeptides created by recombinant-DNA methods or synthesized in whole or in part in vitro. In particular, synthetic polypeptides are contemplated in which 1 or 2 amino acids differ from those set forth in the preferred sequences set forth below.

For the purposes of the present application, "pure form" or "purified form," when used to refer to the protein of interest disclosed herein, shall mean substantially free of other proteins which are not the protein of interest. Preferably, the protein of the present invention is at least 50% pure, more preferably 70% pure and even more preferably 80% or 90% pure.

The following proteins, in substantially pure form, have been discovered by the present inventors as useful in such in vitro diagnostics. These include: Protein A, a 105 kd protein of *M. hyopneumoniae;* Protein B, a 90 kd protein of *M. hyopneumoniae;* Protein C, an 85 kd protein of *M. hyopneumoniae;* Protein D, a 70 kd protein of *M. hyopneumoniae;* Protein E, a 43 kd protein of *M. hyopneumoniae*. It should be noted that the molecular weights associated with the proteins disclosed herein are not to be interpreted as absolute values.

It is believed that each of the proteins A through E is a protein present on the surface of the Mycoplasma organism. When intact Mycoplasma cells are lightly treated with a protease (trypsin), each of these proteins exhibits sensitivity to digestion by the protease, indicating their exposure on the cell surface.

Moreover, it is believed that each of these proteins contain one or more specific portions which may serve as an antigenic determinant capable of binding to at least one antibody present in sera of Mycoplasma infected swine. These specific antigenic portions, either singly or in various combinations, would be, therefore, capable of serving as the basis for an in vitro diagnostic assay.

According to certain preferred embodiments, the present inventors have also shown that at least Protein C (an 85 kd protein) and a fragment thereof are useful in vaccine compositions to prevent Mycoplasma infection in animals. It is also believed that the other disclosed proteins and variants thereof can also ellicit an immune response, and may also protect animals from Mycoplasma infection. Such proteins or fragments thereof may be used individually or in a mixture in a vaccine composition.

DNA sequences encoding portions of these proteins are contained on the lambda gtll clones identified herein. The DNA sequences coding for the entire proteins are contained in the same lambda gtll library from which the above clones were derived, and methods are described below that will allow the identification and isolation of such clones.

A portion of the gene encoding polypeptide A (105 kd) is contained on the lambda gtll clone R60b which contains an insert of Mycoplasma DNA of 1.5 kilobases. This fragment can be excised using the restriction endonucleases Kpnl and Sacl which cut in the flanking vector sequences but not within the insert. The corresponding expression plasmid R60b-a has been constructed by insertion of the KDnl/Sacl insertion fragment of the lambda gtll clone into the plasmid vector pSEV6.

A portion of the gene encoding polypeptide B (90 kd) is contained on the lambda gtll clone LMHC1-9 which contains an insert of Mycoplasma DNA of 0.45 kilobases. This fragment can be excised using the restriction endonucleases Kpnl and Sacl which cut in the flanking vector sequences but not within the insert. The corresponding expression plasmid LMHC1-9a has been constructed by insertion of the Kpn/Sac insertion fragment of the lambda gtll clone into the plasmid vector pSEV6.

A portion of the gene encoding polypeptide C (85 kd) is contained on the lambda gtll clone R69 which contains an insert of Mycoplasma DNA of 0.5 kilobases (specifically 522 bases). This fragment can be excised using the restriction endonucleases Kpnl and Sacl which cut in the flanking vector sequences but not within the insert. The corresponding expression plasmid R69b (also designated pSEV6::R69) has been constructed by insertion of the Kpnl/Sacl insertion fragment of the lambda gtll clone into the plasmid vector pSEV6.

A portion of the gene encoding polypeptide D (70 kd) is contained on the lambda gtll clone 86-4 which contains an insert of Mycoplasma DNA of 3.2 kilobases. This fragment can be excised using the restriction endonucleases KpnI and SauI which cut in the flanking vector sequences but not within the insert. The corresponding expression plasmid 86-4C has been constructed by insertion of the KpnI/SauI insertion fragment of the lambda gtll clone into the plasmid vector pSEV6.

A portion of the gene encoding polypeptide E (43 kd) is contained on the lambda gtll clone P1 which contains an insert of Mycoplasma DNA of 0.5 kilobases. This fragment can be excised using the restriction endonucleases KpnI and SacI which cut in the flanking vector sequences but not within the insert. The corresponding expression plasmid Plc has been constructed by insertion of the KpnI/SacI insertion fragment of the lambda gtll clone into the plasmid vector pSEV6.

Various methods may be used to express the DNA encoding the proteins or the proposed antigenic determinants. In particular, it is contemplated that the DNA contained on the lambda gtll phage clones may be expressed in mammalian systems.

In an alternate preferred embodiment, the DNA of interest is excised from the DNA contained on the lambda gtll phage clone and inserted, in a suitable form, into a microbial expression system. In this embodiment, the antigenic polypeptides are produced by a method comprising:

(a) preparation of a DNA sequence coding for a polypeptide possessing antigenic properties analogous to those possessed by a polypeptide produced by Mycoplasma organisms;

(b) cloning the DNA sequence into a vector capable of being transferred into and replicating in a host microorganism, such vector containing operational elements for the DNA sequence;

(c) transferring the vector containing the DNA sequence and operational elements into a host microorganism capable of expressing the antigenic polypeptides;

(d) culturing the host microorganism under conditions appropriate for amplification of the vector and expression of the polypeptide; and (e) in either order:

(i) harvesting the polypeptide; and (ii) causing the polypeptide to assume a structure whereby it possesses antigenic properties analogous to properties possessed by polypeptides produced by Mycoplasma organisms.

Since *M. hyopneumoniae* is a prokaryote, genomic DNA may be used directly without concern about introns. However, other Mycoplasma species have been shown to utilize the normal stop codon UGA as a tryptophan codon in protein synthesis. As this is also true in *M. hyopneumoniae* (See Example VIII-E), expression in other systems (e.g., *E. coli*) results in premature termination during protein synthesis when this codon is read as a stop. Whether this occurs for the proteins of interest can be determined by growing the expression vector in suitable tRNA suppressor strains. If premature termination does occur, it will be possible to correct the problem by DNA sequencing the area containing the UGA codon and substituting the proper codon by site-directed mutagenesis. The present inventors have provided procedures to accomplish substitution of the UGA codons to prevent premature termination. See Example IX-A.

The DNA prepared in accordance with the above methods is inserted into an expression vector suitable for use in the intended expression system. Embodiments of the present invention are envisioned as employing other known or currently undiscovered vectors which would contain one or more of the DNA sequences encoding antigenic polypeptides described herein. In particular, it is preferred that these vectors have some or all of the following characteristics: (1) possess a minimal number of host-organism sequences; (2) be stable in the desired host; (3) be capable of being present in a high copy number in the desired host; (4) possess a regulatable promoter; and (5) have at least one DNA sequence coding a selectable trait present on a portion of the plasmid separate from that where DNA sequence encoding for the antigenic polypeptide will be inserted.

The following, noninclusive, list of cloning vectors is believed to set forth vectors which can easily be altered to meet the above-criteria and are, therefore, preferred for use in the present invention. Such alterations are easily performed by those of ordinary skill in the art in light of the available literature and the teachings herein.

TABLE I

| Hosts | Vectors | Comments |
|---|---|---|
| *E. coli* | pUC8 | Many selectable replicons |
| | pUC9 | have been characterized. |
| | pBR322 | Maniatis, T. et al. (1982) |
| | pGW7 | Molecular Cloning: A |
| | placIq | Laboratory Manual, Cold |
| | pDP8 | Spring Harbor Laboratory. |
| | PTAC | |
| | pBR325 | |
| | pUC18 | |
| | pSEV6 | |
| | M13mp18 | |
| | M13mp19 | |
| BACILLUS | pUB110 | Genetics and Biotechnology |
| *B. subtilis* | pSA0501 | of Bacilli, Ganesan and |
| *B. amyloliquefaciens* | pSA2100 | Hoch, eds., 1984, Academic Press. |
| *B. stearothermophilus* | pBD6 | |
| | pBD8 | |
| | pT127 | |
| PSEUDOMONAS | RSF1010 | Some vectors useful in broad host range of gram- |
| *P. aeruginosa* | Rms149 | negative bacteria including |
| *P. putida* | pKT209 | Xanthomonas and Agrobacterium. |
| | RK2 | |
| | pSa727 | |
| CLOSTRIDIUM | pJU12 | Shuttle plasmids for *E.* |
| *C. perfringens* | pJU7 | *coli* and *C. nerfrincrens* |
| | pJU10 | construction ref. Squires, |
| | pJU16 | C. et al. (1984) Journal |
| | pJU13 | Bacteriol. 159:465-471. |
| SACCHAROMYCES | YEP24 | Botstein and Davis in Molecular Biology of the |
| *S. cerevisiae* | YIp5 | Yeast Saccharomyces, |
| | YRp17 | Strathern, Jones, and Broach, eds., 1982, Cold Spring Harbor Laboratory. |

It is to be understood that additional cloning vectors may now exist or will be discovered which have the above-identified properties and are therefore suitable for use in the present invention. These vectors also are contemplated as being within the scope of the disclosed series of cloning vectors into which the DNA sequences encoding the antigenic polypeptides may be introduced, along with any necessary operational elements, and which altered vector is then included within the scope of the present invention and would be capable of being used in the recombinant-DNA method set forth more fully below.

These operational elements, as discussed herein, include but are not limited to at least one promoter, at least one ribosome-binding sequence and at least one transcription terminator. Preferably, these "operational elements" also include at least one operator, at least one leader sequence for proteins to be exported from the intracellular space, at least one regulator and any other DNA sequences necessary or preferred for appropriate transcription and subsequent translation of the vector DNA.

In addition to the above list, an *E. coli* vector system is preferred in one embodiment as a cloning vector. Moreover, several vector plasmids which autonomously replicate in a broad range of Gram negative bacteria are preferred for use as cloning vehicles in hosts of the genera Pseudomonas. These are described by Tait, R. C., Close, T. J., Lundquist, R. C., Hagiya, M., Rodriguez, R. L., and Kado, C. I. in *Biotechnology*, May, 1983, pp. 269–275; Panopoulos, N. J. in *Genetic Engineering in the Plant Sciences*, Praeger Publishers, New York, New York, pp. 163–185, (1981); and Sakaguchi, K. in *Current Topic in Microbiology and Immunology*, 96:31–45, (1982).

One particularly preferred construction employs the plasmid RSF1010 and derivatives thereof as described by Bagdasarian, M., Bagdasarian, M. M., Coleman, S., and Timmis, K. N. in *Plasmids of Medical, Environmental and Commercial Importance*, Timmis, K. N. and Puhler, A , eds., Elsevier, North Holland Biomedical Press, (1979). The advantages of RSF1010 are that it is relatively small, high copy number plasmid which is readily transformed into and stably maintained in both *E. coli* and Pseudomonas species. In this system, it is preferred to use the Tac expression system as described for Escherichia, since it appears that the *E. coli* trp promoter is readily recognized by Pseudomonas RNA polymerase as set forth by Sakaguchi, K. in Current Topics in *Microbiology and Immunology*, 96:31–45 (1982) and Gray, G. L., McKeown, K. A., Jones, A. J. S., Seeburg, P. H., and Heyneker, H. L. in *Bio/Technology*, February 1984, pp. 161–165. Transcriptional activity may be further maximized by requiring the exchange of the promoter with, e.g., an *E. coli* or *P. aeruginosa* trp promoter.

In a preferred embodiment, *P. aeruginosa* is transformed with vectors directing the synthesis of the antigenic polypeptides as either an intracellular product or as a product coupled to leader sequences that will effect its processing and export from the cell. In this embodiment, these leader sequences are preferably selected from the group consisting of beta-lactamase, OmpA protein, and that of carboxypeptidase G2 from Pseudomonas. Translation may be coupled to translation initiation for any of the *E. coli* proteins as well as to initiation sites for any of the highly expressed proteins of the host to cause intracellular expression of the antigenic polypeptides.

In those cases where restriction minus strains of a host Pseudomonas species are not available, transformation efficiency with plasmid constructs isolated from *E. coli* are poor. Therefore, passage of the Pseudomonas cloning vector through an r– m+ strain of another species prior to transformation of the desired host is desired, as set forth in Bagdasarian, M., et al., *Plasmids of Medical, Environmental and Commercial Importance*, pp. 411–422, Timmis and Puhler eds., Elsevier/North Holland Biomedical Press (1979).

Furthermore, a preferred expression system in hosts of the genera Bacillus involves using plasmid pUB110 as the cloning vehicle. As in other host vector systems, it is possible in Bacillus to express the antigenic polypeptides of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering*, Vol. 2, Setlow and Hollander eds., Plenum Press, New York, N.Y., pp. 115–131, (1980). For the expression and secretion of antigenic polypeptides from *B. subtilis*, the signal sequence of alpha-amylase is preferably coupled to the coding region for the antigenic polypeptide. For synthesis of intracellular polypeptides, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilli*, Ganesau, A. T. and Hoch, J. A., eds., Academic Press, pp. 249–263, (1984). The lacI gene of lacI$^q$ also would be included to effect regulation.

One preferred construction for expression in Clostridium is in plasmid pJU12 described by Squires, C. H. et al in *J. Bacteriol.*, 159:465–471 (1984), transformed into *C. perfringens* by the method of Heefner, D. L. et al. as described in *J. Bacteriol.,* 159:460–464 (1984). Transcription is directed by the promoter of the tetracycline resistance gene. Translation is coupled to the Shine-Dalgarno sequences of this same $tet^r$ gene in a manner strictly analogous to the procedures outlined above for vectors suitable for use in other hosts.

Maintenance of foreign DNA introduced into yeast can be effected in several ways. See, for example, Botstein, D., and Davis, R. W., in *The Molecular Biology of the Yeast Saccharomyces*, Cold Spring Harbor Laboratory; Strathern, Jones and Broach, eds., pp. 607–636 (1982). One preferred expression system for use with host organisms of the genus Saccharomyces harbors the antigenic polypeptide gene on the 2 micron plasmid. The advantages of the 2 micron circle include relatively high copy number and stability when introduced into cir° strains. These vectors preferably incorporate the replication origin and at least one antibiotic resistance marker from pBR322 to allow replication and selection in *E. coli.* In addition, the plasmid will preferably have 2 micron sequences and the yeast LEU2 gene to serve the same purposes in LEU2 mutants of yeast.

The regulatable promoter from the yeast GAL1 gene will preferably be adapted to direct transcription of the antigenic polypeptide gene. Translation of the DNA sequence in yeast will be coupled to the leader sequence that directs the secretion of yeast alpha-factor. This will cause formation of a fusion protein which will be processed in yeast and result in secretion of the desired antigenic polypeptide. Alternatively, a methionyl-antigenic polypeptide will be translated for inclusion within the cell.

As will be seen from an examination of the individual cloning vectors and systems contained in Table I and description, various operational elements may be present in each of the preferred vectors of the present invention. It is contemplated any additional operational elements which may be required may be added to these vectors using methods known to those of ordinary skill in the art, particularly in light of the teachings herein.

In practice, it is possible to construct each of these vectors in a way that allows them to be easily isolated, assembled, and interchanged. This facilitates assembly of numerous functional genes from combinations of these elements and the coding region of the antigenic polypeptide. Further, many of these elements will be applicable in more than one host.

At least one origin of replication recognized by the contemplated host microorganism, along with at least one selectable marker and at least one promoter sequence capable of initiating transcription of the DNA encoding for the antigenic polypeptide are contemplated as being included in these vectors. It is additionally contemplated that the vectors, in certain preferred embodiments, will contain DNA sequences capable of functioning as regulators ("operators"), and other DNA sequences capable of coding for regulator proteins. In preferred vectors of this series, the vectors additionally contain ribosome binding sites, transcription terminators and leader sequences.

These regulators, in one embodiment, will serve to prevent expression of the DNA sequence encoding for the antigenic polypeptide in the presence of certain environmental conditions and, in the presence of other environmental conditions, allow transcription and subsequent expression of the protein coded for by the DNA sequence. In particular, it is preferred that regulatory segments be inserted into the vector such that expression of the DNA sequence will not occur in the absence of, for example, isopropylthio-beta-d-galactoside. In this situation, the transformed microorganisms containing the DNA of interest may be grown to a desired density prior to initiation of the expression of the antigenic polypeptides. In this embodiment, expression of the desired antigenic polypeptide is induced by addition of a substance to the microbial environment capable of causing expression of the DNA sequence after the desired density has been achieved.

Additional operational elements include, but are not limited to, ribosome-binding sites and other DNA sequences necessary for microbial expression of foreign proteins. The operational elements as discussed herein can be routinely selected by those of ordinary skill in the art in light of prior literature and the teachings contained herein. General examples of these operational elements are set forth in B. Lewin, Genes., Wiley & Sons, New York (1983). Various examples of suitable operational elements may be found on the vectors discussed above and may be elucidated through review of the publications discussing the basic characteristics of the aforementioned vectors.

In one preferred embodiment of the present invention, an additional DNA sequence is located immediately preceding the DNA sequence which codes for the antigenic polypeptide. The additional DNA sequence is capable of functioning as a translational coupler, i.e., it is a DNA sequence that encodes an RNA which serves to position ribosomes immediately adjacent to the ribosome binding site of the antigenic polypeptide RNA with which it is contiguous.

Upon synthesis and/or isolation of all necessary and desired component parts of the above-discussed cloning vectors, the vectors are assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth in Schonert et al., *Proceedings of the National Academy of Sciences U.S.A.*, 81:5403–5407 (1984).

In construction of the cloning vectors of the present invention, it should additionally be noted that multiple copies of the DNA sequence encoding for the antigenic polypeptide and its attendant operational elements may be inserted into each vector. In such an embodiment, the host organism would produce greater amounts per vector of the desired antigenic polypeptides. The number of multiple copies of the DNA sequence which may be inserted into the vector is limited only by the ability of the resultant vector, due to its size, to be transferred into and replicated and transcribed in an appropriate host microorganism.

Additionally, it is preferred that the cloning vector contain a selectable marker, such as a drug resistance marker or other marker which causes expression of a selectable trait by the host microorganism. Such a drug resistance or other selectable marker is intended in part to facilitate in the selection of transformants. Additionally, the presence of such a selectable marker on the cloning vector may be of use in keeping contaminating microorganisms from multiplying in the culture medium. In this embodiment, such a pure culture of the transformed host microorganisms would be obtained by culturing the microorganisms under conditions which require the induced phenotype for survival.

It is noted that, in a preferred embodiment, it is also desirable to reconstruct the 3' end of the coding region to allow assembly with 3' non-translated sequences. Included among these non-translated sequences are those which stabilize the mRNA or enhance its transcription and those that provide strong transcriptional termination signals which may stabilize the vector as they are identified by Gentz, R., Langner, A., Chang, A. C. Y., Cohen, S. H., and Bujard, H. in *Proc. Natl. Acad. Sci. U.S.A.*, 78:4936–4940 (1981).

The vector thus obtained is then transferred into the appropriate host microorganism. It is believed that any microorganism having the ability to take up exogenous DNA and express those genes and attendant operational elements may be chosen. It is preferred that the host microorganism be an anaerobe, facultative anaerobe or aerobe. Particular hosts which may be preferable for use in this method include yeasts and bacteria. Specific yeasts include those of the genus Saccharomyces, and especially *Saccharomyces cerevisiae*.

Specific bacteria include those of the genera Bacillus and Escherichia and Pseudomonas. Various other preferred hosts are set forth in Table I, supra. In other, alternatively preferred embodiments of the present invention, *Bacillus subtilis, Escherichia coli* or *Pseudomonas aeruginosa* are selected as the host microorganisms.

After a host organism has been chosen, the vector is transferred into the host organism using methods generally known by those of ordinary skill in the art. Examples of such methods may be found in *Advanced Bacterial Genetics* by R. W. Davis et al., Cold Spring Harbor Press, Cold Spring Harbor, N.Y., (1980). It is preferred, in certain embodiments, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the synthetic genes.

If it is contemplated that the recombinant antigenic polypeptides will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of the antigenic polypeptide.

The host microorganisms are cultured under conditions appropriate for the expression of the antigenic polypeptide. These conditions are generally specific for the host organism, and are readily determined by one of ordinary skill in the art, in light of the published literature regarding the growth conditions for such organisms, for example *Bergey's Manual of Determinative Bacteriology*, 8th Ed., Williams & Wilkins Company, Baltimore, Md.

Any conditions necessary for the regulation of the expression of the DNA sequence, dependent upon any operational elements inserted into or present in the vector, would be in effect at the transformation and culturing stages. In one embodiment, the cells are grown to a high density in the presence of appropriate regulatory conditions which inhibit the expression of the DNA sequence encoding for the antigenic polypeptide. When optimal cell density is approached, the environmental conditions are altered to those appropriate for expression of the DNA sequence. It is thus contemplated that the production of the antigenic polypeptide will occur in a time span subsequent to the growth of the host cells to near optimal density, and that the resultant antigenic polypeptide will be harvested at some time after the regulatory conditions necessary for its expression were induced.

The transcription terminators contemplated herein serve to stabilize the vector. In particular, those sequences as described by Gentz et al., in *Proc. Natl. Acad. Sci., U.S.A.* 78: 4936–4940 (1981), are contemplated for use in the present invention.

A clone containing the entire gene for Protein C (pUC18::28C2) has been isolated and sequenced. The insert from clone R69 was used as a DNA hybridization probe to isolate a plasmid clone called pUC18::28C2 was made by inserting *M. hyopneumoniae* DNA, partially digested with the restriction enzyme Sau3a, into the plasmid vector pUC18 cut with BamH1. (See Example VIII). The entire gene and part of the surrounding DNA was sequenced (See Example VIII-B and FIG. 2).

In order to determine the position of the gene within the region sequenced, the amino terminal sequence of the intact Protein C, purified from *M. hyopneumoniae* cells, was determined to give a stating point (See Example VIII-C). In addition, the amino acid sequence was determined for several peptide fragments of Protein C, which were generated by Endopeptidase digestion and purified by HPLC (See Example VIII-D). The sequences of these peptides are shown in FIG. 3. These amino acid sequences were used to determine the proper reading frame of the DNA sequence. The translated DNA sequence for the entire Protein C is shown in FIG. 4, with the positions of the sequenced peptides underlined.

The amino terminal sequence of the intact Protein C was found to lie in the middle of an extensive open reading frame. It appears that the gene for Protein C actually codes for a larger protein (as much as 20 kd larger) which may be processed to the 85 kd size. Since mature Protein C (85 kd) has been determined to be protective, the present inventors have not studied extensively the region which is thought to be processed away. The gene for Protein C (85 kd) (excluding the processed portion) encodes a protein which is 624 amino acids in length, with a calculated molecular weight of 70.5 kd. The discrepancy between the calculated and apparent molecular weights as determined by SDS-PAGE is not unusual. The gene for Protein C contains three in-frame UGA codons (shown boxed in FIG. 4) TGA in the DNA, which code tryptophan (See Example VIII-E). The use of UGA as a tryptophan codon is common among the mycoplasmas, but in other organisms (including *E. coli*) UGA is used as a translation termination signal. To express Protein C in *E. coli*, the UGA codons were changed to *E. coli* UGG (tryptophan) codons (See the discussion below and Example IX).

The original clone for Protein C, R69, is contained completely within the coding sequence for Protein C, starting at nucleotide 455 and extending to nucleotide 976 in the sequence shown in FIG. 4.

Expression clones were made that produce recombinant Protein C. A recombinant plasmid (pT5T::M852) was constructed which expressed the entire Protein C (85 kd) in *E. coli*. Expression of the entire Protein C in an *E. coli* expression vector required the replacement of the three inframe UGA codons with UGG codons, the normal tryptophan codon in *E. coli*. Operationally, this was acheived by replacing the final "A" with a "G" in each of these codons. This was accomplished using a technique called "site directed in vitro mutagenesis" (Kunkel et al., *Methods in Enzymol.*, 154, 367–382 (1987)) whereby a short oligonucleotide is synthesized which is exactly complementary to the region except for the nucleotide to be changed. This position contains a nucleotide which is the complement of the desired substitution. There is enough exact complementarity on either side of the substitution so that the oligonucleotide will anneal to a single stranded vector containing the unaltered sequence. When a second strand is synthesized using the oligonucleotide as a primer, the alteration is incorporated and subsequent replication yields DNA molecules with both strands substituted. This technique was used to change all three of the UGA codons to UGG in the gene for Protein C (See Example IX-A).

In order to identify a specific protective protein or proteins, an actual efficacy test (protection of swine against *Mycoplasma hyopneumoniae* infection) was used as an assay for the detection and eventual purification of a specific protective protein. Starting with relatively crude extracts which showed some protection, individual protein components were purified and tested, resulting in the identification of Protein C as a protective protein. The cloning and expression of recombinant versions of Protein C (a full length and a truncated version) which were also protective prove conclusively that Protein C is a protective agent.

A variety of protein extracts and purified proteins were tested as vaccines. These included:

S1: An extract of proteins released from whole *Mycoplasma hyopneumoniae* cells when subjected to low pH conditions. (Described in Example X-A2).

7S: Proteins present in the S1 extract which remain soluble when the pH is raised to 7.0. (Described in Example X-A3). Can be denatured by adding SDS to 1.25% or urea to 6M.

PROTEIN C (NATURAL 85 kd PROTEIN) : Purified from S1 or 7S extracts by methods described in Example X-B.

FULL LENGTH RECOMBINANT PROTEIN C: Described in Example IX and X-C.

TRUNCATED RECOMBINANT PROTEIN C: Described in Section IX and X-D.

It is to be understood that application of the teachings of the present invention to a specific problem or environment will be within the capabilities of one having ordinary skill in the art in light of the teachings contained herein. Examples of the products of the present invention and representative processes for their isolation and manufacture appear in the following examples. It should be noted that all literature references used to further elucidate these examples are specifically incorporated herein by reference.

EXAMPLES

The literature articles cited herein are incorporated by reference in their entirety.

I. CONSTRUCTION OF THE LAMBDA GT11 EXPRESSION LIBRARY

A. CONSTRUCTION OF THE M. HYOPNEUMONIAE GENOMIC DNA EXPRESSION LIBRARY

The rationale for construction of a genomic expression library was to obtain a representative clone for every antigenically active protein that could be expressed by *M. hyopneumoniae*. Since prokaryotic DNA does not contain introns, it was not necessary to construct a cDNA library to accomplish this. Because of the small genome size, a relatively small number of clones are required to adequately represent the *M. hyopneumoniae* genome. Using 750 kilobase pairs as the estimate of the genome size for *M. hyopneumoniae*, it was calculated that for a 99% probability of having every 100 bp region in both orientations and in all three reading frames, $1.4 \times 10^5$ individual recombinants were required.

In lambda gtll, cloned DNA fragments coding for peptides are expressed as fusion proteins when they are inserted at the unique EcoRI site near the carboxy terminus of the beta-galactosidase gene in the phage. Insertion of foreign DNA in the beta-galactosidase gene inactivates the gene, thus allowing identification of recombinant phages on indicator plates.

The *M. hyopneumoniae* genomic expression library was obtained in four consecutive steps. First, genomic DNA was obtained from *M. hyopneumoniae* cells. Second, random fragments were generated by sonication, the ragged ends were blunted using phage T4 polymerase, internal EcoRI restriction sites were protected by EcoRI methylase, EcoRI linkers were added to the ends and excess linkers cleaved off. Third, the prepared fragments were ligated into the lambda gtll vector DNA (purchased from Vector Cloning Systems, San Diego, Calif.) and packaged in vitro. Finally, the in vitro packaged recombinant phage were amplified.

1. PREPARATION OF GENOMIC DNA FROM *MYCOPLASMA HYOPNEUMONIAE* CELLS

Approximately $10^{11}$ frozen *M. hyopneumoniae* cells were thawed in ice and transferred to a polypropylene tube. The volume of cells was 0.8 ml. To this was added a ml of proteinase K solution: 0.075M Tris pH8; 0.17M EDTA pH8; 0.15% Triton X 100; and 400 ug/ml Proteinase K (BOEHRINGER MANNHEIM BIOCHEMICALS, Indianapolis, Ind.). The cells were incubated with the proteinase K solution at 65° C. for 30 minutes. 2.0 ml of phenol was added to the mixture and the tube was gently rocked at 4° C. for 20 min. The sample was then centrifuged in a BECKMAN JA20 rotor at 5000 rpm for 5 min at 4° C. The aqueous phase was removed with a large bore plastic pipette. The aqueous phase was extracted with 2 ml of a 24:1 mixture of chloroform and isoamyl alcohol, by rocking for 20 min at 4° C., letting the tube stand 5 min for the phases to separate, and then removing the aqueous phase with a large bore plastic pipette.

The aqueous phase was then re-extracted with phenol followed by chloroform/isoamyl alcohol as described in the above paragraph. The extracted aqueous phase was adjusted to 0.3M sodium acetate by adding a 1/10 volume of a 3.0M sodium acetate stock solution. DNA was precipitated from this solution by adding 2.5 volumes of cold ethanol. Gentle mixing with the ethanol yielded a large, viscous mass of nucleic acid that was "spooled" out of solution using a small glass rod. This material was then rinsed twice with 70% ethanol and allowed to air-dry. The dry nucleic acids were resuspended in 0.5 ml of TE buffer by rocking the solution for 16 hr at 4° C.

In order to remove any contaminating RNA from the *M. hyopneumoniae* DNA preparation, the nucleic acids were treated with RNaseA. Five-tenths milliliter of the sporozoite nucleic acid preparation was treated with 2.5 ug/ml of RNaseA (MILES LABORATORIES, Elkhart, Ind.) at 65° C. for 30 min. The aqueous phase was adjusted to 3.2M ammonium acetate by adding a 0.75 volume of a 7.5M stock solution. The DNA was precipitated from this solution with the addition of 0.54 volumes of isopropanol. Mixing of the isopropanol yielded a large viscous pellet that was spooled from the solution and rinsed twice with 80% ethanol. After air drying, the DNA was resuspended in 0.2 ml of TE buffer.

Integrity of the *M. hyopneumoniae* DNA was analyzed by electrophoresis through an agarose gel and subsequent staining of the gel with ethidium bromide. These results indicated that the DNA was of high molecular weight and relatively free of RNA. The concentration of the DNA was determined by optical absorbance at 260 nm. This particular preparation yielded 90 μg of purified DNA.

2. PREPARATION OF SONICATED *M. HYOPNEUMONIAE* GENOMIC DNA FRAGMENTS

In order to have a given fragment from the *M. hyopneumoniae* genome aligned in the proper reading frame for transcription and translation of the native polypeptide, it was decided to generate random fragments by sonication to that all possible frames would be represented.

*M. hyopneumoniae* DNA was sonicated with a small tipped probe of a Branson Sonifier cell disrupter 200 set at the lowest power setting. 80 μg of DNA in 200 μl total volume was sonicated in three 3-second bursts. This generated fragments ranging in size from 0.3 to 23 Kb in size with the highest proportion in the 1.3 to 4.4 Kb range.

The ragged ends generated by the sonication were blunted using T4-DNA polymerase (NEW ENGLAND BIOLABS; Beverly, Mass.). The reaction was carried out in 33 mM Tris Acetate pH7.8; 66 mM Potassium Acetate, 10 mM Magnesium Acetate, 0.1 mg/ml Bovine Serum Albumin, 0.5 mM dithiothreitol, and 0.1 mM of each of the deoxynucleotide triphosphates, dATP, dGTP, dCTP, dTTP. For 65 μg of sonicated DNA, 20 units of T4 polymerase was reacted for 1 hour at 37°. The reaction was stopped by heating the sample for 10 min at 68° C. Excess salts were removed by passing the reaction mix over a BIOGEL P30 (BIO RAD) column equilibrated in TE.

In order to protect any *M. hyopneumoniae* genomic DNA fragments that might have internal EcoRI sites, it was necessary to modify the DNA. EcoRI methylase (NEW ENGLAND BIOLABS) was reacted with the fragmented *M. hyopneumoniae* DNA in the presence of S-adenosyl methionine using conditions recommended by the supplier. The methylase was inactivated by phenol extraction of the reaction mix, and residual phenol was removed by ether extractions. The mix was then adjusted to 0.3M with sodium acetate, and 2.5 volumes of ethanol were added. After 30 min at −70° C., the precipitated DNA was pelleted by centrifugation. This DNA was resuspended in TE buffer.

Short oligonucleotide EcoRI linkers (NEW ENGLAND BIOLABS) were added to the blunt ended fragments in a ligation reaction consisting of 66 mM Tris pH7.6, 5 mM $MgCl_2$, 5 mM dithiothreitol, 10 mMATP, with the linker at 5–10 uM. T4 DNA ligase (P.L. BIOCHEMICALS) was added and the reaction proceeded at 14° C. for 16 hours. The ligation reaction was terminated by heating the mixture at 70° for 10 min.

Sodium chloride was then added to 0.1M, excess EcoRI was added, and the reactions were incubated at 37° C. for several hours. The EcoRI was inactivated by heating at 70° C. for 10 min.

Removal of excess linkers and size fractionation of the DNA fragments was carried out by density centrifugation in a 10 to 40% sucrose gradient in 1M NaCl; 20 mM tris pH8, 5 mM EDTA. The DNA was applied to the top of the gradient and was spun in a BECKMAN SW41 rotor at 26,000 rpm for 24 hours at 15° C.

Fractions were collected in 0.3 ml aliquots. Samples of these were assayed by aqueous gel electrophoresis and staining by Ethidium Bromide to compare the size of the smear of fragments in each fraction with molecular weight markers. Fractions which were enriched for fragments in the 1 to 6 Kb range were pooled, then dialyzed and concentrated using a CENTRICON 30 (AMICON) apparatus.

3. LIGATION OF FRAGMENTS TO LAMBDA gt11 AND IN VITRO PACKAGING OF THE RECOMBINANT DNA

Phosphatased and EcoRI-cleaved lambda gt11 DNA was mixed with the prepared fragments of *M. hyopneumoniae* DNA. These DNAs were ligated with T4 DNA ligase (P.L BIOCHEMICALS) overnight at 14° C. A small aliquot of the ligation reaction mixture was analyzed by gel electrophoresis to monitor the ligation reaction. The mixture was heated at 70° C. for 5 min and then mixed with lambda in vitro packaging extracts (VECTOR CLONING SYSTEMS, San Diego, Calif.). The packaging reaction was allowed to proceed for 60 minutes at room temperature and then a drop of chloroform was added to prevent bacterial growth. Titration of this mix yielded a library with a complexity of $1.5 \times 10^5$ recombinants.

4. AMPLIFICATION OF THE *M. HYOPNEUMONIAE* EXPRESSION LIBRARY

Packaged phage were diluted with lambda dil and adsorbed to *E. coli* strain Y1088 as described by Young, R. and Davis, R. in *Science*, 222:778–782 (1983). Amplification of the library on this strain ensures that the beta-galactosidase gene is not expressed; therefore, any phage containing coding sequences that might be deleterious to the host *E. coli* cell are not expressed and not lost from the library. Amplifications of the library yield a stock that was $6 \times 10^9$ phage per ml.

II. GENERAL METHODOLOGY

A. ANTIBODY SCREENING OF THE LAMBDA GT11: *M. HYOPNEUMONIAE* EXPRESSION LIBRARY

The lambda gt11:*M. hyopneumoniae* expression library was plated at densities of 5,000 through 20,000 phage per 150-mm plate using *E. coli* Y1090 as host as described by Young and Davis in *Science*, 222:778–782, (1983). Plates were incubated at 37° or 42° for 4 hr, then overlaid with nitrocellulose filters (BA-85, SCHLEICHER AND SCHUELL) that had been soaked in 10 mM IPTG and air-dried. After incubating overnight at 37° C., filters were batch-washed 3×10 min in TBS (10 mM Tris-HCl pH 8.0, 150 mM NaCl). Non-specific protein binding sites on the filters were blocked by incubating filters for 60 min in TBS+2% bovine serum albumin (Fraction V, MILES LABORATORIES, Elkhart, Ind.). The filters were then incubated individually or in pairs for 2 hr with 10–20 ml of primary antibody (e.g., immune swine serum, hyperimmune rabbit antimycoplasma serum, mouse monoclonal antimycoplasma antibodies) typically diluted 1:200 (1:500 for monoclonals) with TBS to which had been added 2% bovine serum albumin (BSA). The filters were washed 3×10 min with TBS containing 0.1% NP-40 (SIGMA), then incubated singly or in pairs for 60 min with 10–20 ml solution of a second antibody (e.g., peroxidase-conjugated goat anti-rabbit IgG, CAPPEL LABORATORIES) diluted 1:500 in TBS+ 2% bovine serum albumin. Filters were batch-washed 3×10 min in TBS and stained in a solution comprising 200 ml TBS, 2.5 ml of a 3% hydrogen peroxide solution and 40 ml of a 3 mg/ml solution of 4-chloro-1-napthol in methanol. Staining was quenched by removing the filters to water. Positive staining plaques were subjected to several rounds of rescreening with antibody as described above until pure.

B. ELUTION OF ANTIBODIES BOUND TO PROTEINS IMMOBILIZED ON NITROCELLULOSE MEMBRANES

When proteins are immobilized on nitrocellulose membranes such as Western blot transfers of proteins separated on polyacrylamide gels or replicas of phage plaques taken from agar plates, it is possible to bind antibodies which specifically recognize the immobilized proteins. Antibodies which do not specifically bind to the immobilized proteins remain in solution and can be easily washed away, leaving behind only those specifically bound.

The bound antibodies can be eluted by rinsing the filters in a low pH buffer (5 mM glycine, pH 2.3, 0.5M NaCl, 0.5% Tween 20, 0.01% BSA), which dissociates the antibody-antigen complex. If the eluted antibodies are immediately neutralized, i.e., using a 50 mM Tris HCl, final concentration, they retain full activity and can be used for a variety of analytical purposes.

1. DETERMINATION OF MYCOPLASMA PROTEIN CORRESPONDING TO INSERT CLONE

Antibodies eluted from plaque replicas of a purified recombinant clone were used to determine which Mycoplasma protein corresponded to that clone. By eluting antibodies bound to plaque replicas of the recombinant clones and using those antibodies to probe Western blots of Mycoplasma proteins, it was possible to determine which protein is encoded in the recombinant clone.

Five thousand to ten thousand plaques from a single purified recombinant clone were plated on a 100 mm plate, and a plaque lift was made. The lift filters were washed 3×10 min in TBS and non-specific protein binding was blocked by incubation in TBS+10% BSA for 1 hr. The filters were washed 3×10 min in TBS. A strip 5 mm wide was cut from the filter disc. Polyclonal antimycoplasma serum was bound to the strip, washed and eluted as described above. The eluted antibodies were then used to probe a Western blot of mycoplasma proteins.

III. PLASMID VECTORS FOR EXPRESSION OF FUSION PROTEINS

A number of antigenically reactive M. hyopneumoniae recombinant phage clones were identified in the expression library. Since the lambda gtll lysogens appeared to make a limited quantity of fusion protein, we constructed a plasmid expression vector that would produce the fusion proteins in milligram quantities.

A. pSEV4

Plasmid pLG2 was obtained from Dr. L. Guarente (MIT) (Guarente, L., in Cell, 20:543–553 (1980). This vector is a pBR322 derivative which, like lambda gtll, has lac operator and promoter sequences in addition to a wild-type beta-galactosidase gene containing a single EcoRI site near the 3' end of the gene. In addition, pLG2 contains the lac repressor gene. Moving M. hyopneumoniae DNA inserts from lambda gtll into the EcoRI site of this vector yields an identical fusion protein to that initially identified in the phage.

Plasmid pLG2 was modified to remove an extra EcoRI site prior to its use for expression. Plasmid pLG2 was partially digested with EcoRI restriction endonuclease to linearize the plasmid. The plasmid DNA was then displayed on a preparative agarose gel and the linear-sized DNA band was eluted from the gel. The eluted DNA was precipitated by making the solution 0.3M with sodium acetate and adding 2.5 volumes of ethanol. The DNA was pelleted by centrifugation and the pellet was resuspended in TE buffer. The Klenow fragment of E. coli DNA Polymerase I was mixed with the DNA in the presence of dATP and dTTP to fill in the EcoRI cohesive ends. After heat inactivation at 70° C. for 10 min, T4 DNA ligase (P.L. BIOCHEMICALS) was added and the mixture was incubated at 4° C. for 16 hr. The ligated DNA was then used to transform E. coli AMA1OO4. Casadaban, M., et al., in Methods in Enzymology, 100:293 (1983).

Transformants were selected on ampicillin plates in the presence of a chromagenic substrate for beta-galactosidase activity (X-GAL). Transformants with beta-galactosidase activity were screened by cleaving the DNA with EcoRI. A plasmid, pSEV4, that had only a single EcoRI site near the carboxy-terminus of the beta-galactosidase gene was identified from the transformants and characterized.

Plasmid pSEV4 has a unique EcoRI site near the carboxy-terminus of the beta-galactosidase gene. Plasmid pSEV4 contains the wild-type lac operator, promoter and repressor in addition to the beta-galactosidase gene. Upon induction with IPTG for 60 min, beta-galactosidase activity was increased by 300-fold. Uninduced cells containing pSEV4 produced approximately 1000 units/mg of total cellular protein, whereas IPTG-induced cells gave approximately 300,000 units/mg of total cell protein. Protein gel analysis of induced and uninduced cells also showed the over-production of beta-galactosidase by induced cells. This new plasmid, pSEV4, has been used to express a number of M. hyopneumoniae antigens as fusion proteins.

B. pSEV6

A successor to pSEV4 was constructed to allow polarized "cassette" subcloning of DNA inserts from lambda gtll directly into a plasmid expression vector. Because EcoRI inserts could be subcloned in either orientation of pSEV4, each pSEV4 subclone must be screened for its antigenic reaction. Polarized subcloning using pSEV6 obviates the need for this extra analysis.

Extensive mapping of pSEV4 located five restriction endonuclease sites in the lac operon 5' to the beta-galactosidase gene's unique EcoRI site. Three of these sites are unique and two were made unique by deletion of the superfluous DNA between the lacI gene and the pBR322-derived amp$^r$ gene. Only one useful restriction site was found 3' to the EcoRI site, the NcoI site, therefore, additional restriction enzyme sites were inserted in this region using a chemically synthesized polylinker.

The construction of pSEV6 was done in two steps. First, pSEV4 was shortened by approximately 5,700 bp to eliminate superfluous DNA. Plasmid pSEV4 was cleaved with SphI restriction endonuclease, and the enzyme was inactivated by heating at 70° C. for 10 min. The DNA was then partially digested with AatIII and the resulting digest was displayed by electrophoresis on a preparative agarose gel. The 7,620 bp fragment was excised from the gel and electroeluted.

The electroeluted DNA was precipitated from a 0.3M sodium acetate solution by adding 2.5 volumes of ethanol and incubating at −70° C. for 30 min. The DNA was concentrated by pelleting in a Brinkman microcentrifuge for 15 minutes and the pellet was resuspended in TE buffer. T4 DNA polymerase (NEW ENGLAND BIOLABS) was added to blunt-end the cohesive ends generated by the AatII digest. After heat inactivation of the T4 DNA polymerase, T4 DNA ligase (P.L. BIOCHEMICALS) was added to ligate the blunt ends of the DNA fragment. The ligated DNA was used to transform competent AMA1OO4 E. coli cells. Lac+ transformants were screened for the 7,620 bp plasmid. One plasmid, pSEV5, was identified and characterized as having the appropriate structure.

DNA from pSEV5 was purified by standard methods, and subsequently cleaved with the restriction endonuclease NcoI, which cleaved at a unique site 3' of the beta-galactosidase gene. An oligonucleotide adapter molecule would regenerate the NcoI site and which also contained BglII and Kpn I sites was chemically synthesized. The sequence of this adapter molecule is as follows:

5'-GTAAGGAGGAATAACATATGGAATTCGAG-3'
3'-ACGTCATTCCTCCTTATTGTATACCT-
TAAGCTCCTAG-5'

This oligonucleotide was ligated to the NcoI cleaved pSEV5 with T4 DNA ligase (P.L. BIOCHEMICALS). The ligated DNA was used to transform competent E. coli AMA1OO4 cells. DNA from the resulting lac+ transformants was screened for the presence of the unique KpnI and NcoI sites. A plasmid was identified from this screen with all of the designed sequences. This plasmid, pSEV6, has been used for expression of various of the antigenically reactive fusion proteins.

IV. PURIFICATION OF RECOMBINANT FUSION PROTEINS

The beta-galactosidase::M. hyopneumoniae antigen fusion proteins have been purified either by use of a substrate analog affinity column for beta-galactosidase or by classical methods of protein purification.

A. Preparation of Extracts

Two liters of Luria broth, pH 7.5, containing 50 ug/mL of ampicillin were inoculated with 10–20 ml of an overnight culture of E. coli AMA1OO4 containing one of the recombinant plasmids. The cells were allowed to grow at 37° C. to mid-log phase ($A_{600}$=0.2). Isopropyl-thiogalactoside (IPTG) was added to a final concentration of 1 mM to induce formation of the fusion protein. The cells were allowed to grow out for 2 hours, and then harvested by centrifugation at 5000×G for 15 min at 4° C. All subsequent operations were carried out at 4° C.

The cells were resuspended in 20 mL of breaking buffer (50 mM Tris-HCl, pH 7.5, 250 mM NaCl, 10 mM $MgCl_2$, 5% glycerol, 1 mM phenymethyl sulfonyl fluoride (PMSF)) at 4° C. and centrifuged again at 5000×G for 15 min. The cells were again suspended in 20–40 mL of breaking buffer. The cells could be frozen at this point and stored at −20° C. if desired.

The unfrozen or thawed cells were broken with two passes through a French pressure cell (AMINCO) at 20,000 psi. Cell debris was removed by centrifugation at 30,000×G for 30 min. Further clarification of the extract could be obtained at this point by ultracentrifugation at 100,000×G for 30 min. The fusion protein was then precipitated by the addition of ammonium sulfate to a final concentration of 20 to 40% saturation. The optimal concentration of ammonium sulfate required for precipitation of the fusion protein varies with the individual protein and must be determined experimentally, using for example, procedures set forth in Heppel, L. in *Methods in Enzymology*, 1:570–576 (1955).

The precipitate solution was stirred for one hour and the precipitate was removed by centrifugation at 30,000×G for 15 min. The pellet was redissolved in 10 to 15 ml of starting buffer (50 mM Tris-HCl, pH 7.5, 250 mM NaCl, 10 mM $MgCl_2$, 1 mM dithiothreitol (DTT) and 0.1% Triton X-100), and then dialyzed overnight against 500 mL of starting buffer.

1. AFFINITY PURIFICATION PROCEDURE

The use of a beta-galactosidase affinity column is based on the method described by Steers and Cuatrecasas in *Methods in Enzymology*, 34:350–358 (1974). Affinity resin (p-aminophenyl-beta-D-Thiogalactopyranoside-agarose, obtained from SIGMA) was packed into a 1.5 cm diameter by 15 cm column. The column was washed with 10 column volumes of starting buffer of 50 mM Tris-HCl, pH 7.5, 250 mM NaCl, 10 mM $MgCl_2$, and 1.0 mM dithiothreitol (DTT) and 0.1 Triton-X100 before use. The column can be regenerated after use by washing extensively with elution buffer 0.1 sodium borate, pH 10.0, 250 mM NaCl, 1 mM DTT or by washing with 6M guanidine hydrochloride in 50 mM Tris-HCl, pH 7.5. After washing, the column is reequilibrated with 10 column volumes of starting buffer.

For affinity chromatography, dialyzed material was applied to the pre-equilibrated affinity column at a flow rate of about 0.2 ml/min. After the sample was applied to the column, the column was washed with 15 ml of starting buffer at the same flow rate, then with 30 ml of starting buffer at about 0.5 ml/min followed with 180 ml starting buffer at about 1 ml/min. Finally, the column was washed with 120 ml of starting buffer without TRITON at the same flow rate.

The absorbed protein was eluted with 0.1 sodium borate, pH 10.0, 250 mM NaCl, 1 mM DTT using 120 ml at a flow rate of about 1 ml/min. The peak-protein containing fractions were pooled and could be concentrated if desired to about 10 ml using an AMICON ultrafiltration device (Model 8050) containing an YM-30 membrane.

2. ULTRACENTRIFUGE PURIFICATION

An alternative purification usable for some of the fusion proteins (e.g., pSEV4::CH2-13) is accomplished by obtaining dialyzed protein as set forth above. The dialyzed material is subjected to ultracentrifugation at 100,000×G for 30 min. The pellet containing the bulk of the fusion protein was redissolved in a small volume of dialysis buffer 50 mM Tris-HCl, ph 7.5, 250 mM NaCl, 10 mM MgCl2 and 1.0 mM dithiothreitol (DTT) and 0.1M TRITON-X 100. This method yields material that is not as pure as that generated by the affinity column when judged by SDS-polyacrylamide electrophoresis.

3. ANALYSIS

The purified materials obtained by these methods were analyzed for protein by the BIO-RAD (Richmond, Calif.) protein method as recommended by the manufacturer. It was also subjected to analysis by SDS-polyacrylamide electrophoresis. These gels are visualized either by protein staining or by Western blot analysis. Protein staining was typically done with either the silver stain method as described by Wray, W. P. et al. in *Anal. Biochem.*, 118:197–203 (1981) or the BIO-RAD protein stain. Western blot analysis is carried out as described by Remart, J. et al. in *PNAS (U.S.A.).*, 76:3116 (1979).

The Western blot analysis involves electrophoretic transfer of the resolved protein bands to nitrocellulose, blocking the nitrocellulose paper with BSA, probing with a specific antibody (either anti-betagalactosidase or anti-mycoplasma sera). After washing, the blots are probed with the appropriate peroxidase conjugated second antibody, followed by color development using the peroxidase catalyzed reaction.

V. GENERAL PROCEDURES FOR OBTAINING THE ENTIRE M. HYOPNEUMONIAE GENE ENCODED BY A FUSION PROTEIN CLONE

The recombinant M. hyopneumoniae* clones that were picked as reactive with various antimycoplasma sera contain only a portion of the entire coding region for that particular polypeptide, because of the requirement that the insert sequence be in frame with the beta-galactosidase gene in lambda gtll and the limited number of clones screened. In some cases it may be important to have cloned the entire coding sequence of a given antigenic *M. hyopneumoniae* polypeptide in order to maximize the immune response or modulate the response. A method is outlined below that will allow the isolation of clones containing such full length fragments.

The lambda gtll expression library described above, may also be viewed as a simple genomic library if one does not require that the inserted segments of *M. hyopneumoniae* be expressed as fusion proteins. Some of these clones should contain the entire coding region for a particular protein even though it is not in frame with the beta galactosidase expression system.

These clones may be detected using DNA hybridization probes derived from the clones already picked by antibody methods and known to correspond to particular mycoplasma proteins. The insert fragments from these clones is "nick translated" using *E. coli* DNA polymerase to incorporate $^{32}$P-labeled deoxynucleotides into the DNA. This labeled DNA is then used as a radioactive probe to select an homologous *M. hyopneumoniae* sequence from the recombinant lambda gt11 library. Phages selected from the recombinant library by this method are plaque purified, DNA is prepared, and the *M. hyopneumoniae* specific insert is mapped with various restriction endonucleases. The resulting map is compared with a similar map derived from the initial clone to confirm the identity of the new genomic phage.

Because there are no introns in the prokaryotic genes, one can determine, from the size of the protein encoded, how much DNA to either side of the labeled DNA must be included to be sure that the entire gene is included. The entire gene may not be contained in a single clone; however, it is possible for anyone skilled in the art to obtain the entire gene. This could be done by "walking" along the *M. hyopneumoniae* genome by isolating phages that contain flanking *M. hyopneumoniae* genomic DNA using the method by Bender, E. et al. in *J. Mol. Biol.*, 168:17–33 (1983). The present inventors have provided the entire gene for Protein C using methods similar to those discussed above. See Example VIII.

VI. PROCEDURES FOR IDENTIFICATION OF CLONES CORRESPONDING TO SURFACE PROTEINS

Proteins which are exposed on the surface of a mycoplasma cell have been shown to be susceptible to digestion by a protease such as trypsin when whole, intact cells are lightly treated with that enzyme (Klinkert, M., Herrmann, R., and Schaller, H., *Infection and Immunity*, 49; 329–335 (1985)). This technique, in combination with the elution of antibodies from clones, allows the rapid determination of whether a particular clone corresponds to a trypsin sensitive surface protein. Total proteins from trypsinized and non-trypsinized mycoplasma cells are placed in adjacent lanes and separated by SDS polyacrylamide slab gel electrophoresis. The displayed proteins are then electroblotted onto nitrocellulose membrane by the western blot procedure. This blot is then probed using antibodies from a polyclonal serum which have been affinity purified from a specific clone using the antibody elution technique described above in Example II-B.

The specific mycoplasma protein on the Western blot corresponding to the clone will be revealed by staining of the bound antibody in the lane with proteins from non-trypsinized cells, showing up as a specific stained band. If that protein is trypsin sensitive, the corresponding position in the lane with proteins from trypsinized cells will be blank, whereas a non-trypsin sensitive band will stain as in the untreated cells. The present inventors have shown trypsin sensitivity for Proteins A, B. C, D and E, indicating that they are surface proteins.

VII. DNA SEQUENCE OF CLONE R69, WHICH ENCODES PART OF PROTEIN C

The recombinant DNA lambda gt11 clone R69 encodes part of protein C. The *M. hyopneumoniae* DNA insert in this clone was sequenced. The insert in this clone was excised with EcoRI and subcloned into the single stranded sequencing vector M13mp18 (See Example VIII-B for references to this vector and sequencing procedures). Subclones with the insert in each orientation were isolated and the sequence determined in both directions.

The 5'→3' orientation of the R69 insert and the proper reading frame were determined by sequencing directly from the double stranded lambda gt11-R69 clone (Chen and Seeburg, DNA, 4:165(1985)) using lambda gt11 forward and reverse primers (NEW ENGLAND BIOLABS).

The DNA insert in this clone is 522 nucleotides long and encodes 173 amino acids. The DNA sequence and translated amino acid sequence which comprises part of protein C are depicted in FIG. 1. This DNA sequence is contained entirely within the coding sequence of Protein C, starting at nucleotide 455 and extending to nucleotide 976 in the sequence of the whole gene shown in FIG. 4.

VIII. ISOLATION OF CLONE pUC18::28C2 AND SEQUENCING OF GENE FOR PROTEIN C

A. ISOLATION OF CLONE pUC18::28C2, CONTAINING THE GENE FOR PROTEIN C

1. CONSTRUCTION OF THE pUC18 GENOMIC LIBRARY

The pUC18 *M. hyopneumoniae* genomic library was constructed to provide a recombinant library with larger insert fragments than the lambda gt11 library (Example I), so that the entire Protein C gene would be contained on a single clone.

Genomic *Mycoplasma hyopneumoniae* DNA was partially digested with the restriction endonuclease Sau3a and size fractionated on a 35 ml 10→40% Sucrose gradient in 1M NaCl, 0.02M Tris pH 8, 0.005 M EDTA. The digested DNA sample was layered on top of the gradient and centrifuged at 100,000×g for 24 hours. One ml fractions were collected from the bottom of the gradient and samples from selected fractions were electrophoresed on a 0.5% agarose gel in TAE buffer (0.04M Tris Acetate, 0.001M EDTA) alongside DNA size standards and stained with Ethidium Bromide to determine the size range of DNA fragments in each fraction. Fractions enriched for DNA fragments in the 8–12 kilo basepair range were pooled, concentrated and dialyzed against TE8 buffer (0.01M Tris, 0.001M EDTA pH 8).

The vector, pUC18, was prepared by complete digestion with the restriction endonuclease BamH1, followed by dephosphorylation with the enzyme Calf Intestinal Phosphatase (0.01 Units of BOEHRINGER-MANNHEIM Calf Intestinal Phosphatase per pmol of vector, 2×30 min at 37° C., in CIP buffer 1 mM ZnCl$_2$, 1 mM MgCl$_2$, 10 mM Tris Cl pH 8.3). This treatment was followed by phenol extraction, ethanol precipitation and resuspension in TE8 buffer.

Four hundred and fifty (450) ng of the size selected genomic fragments was ligated into 50 ng of the BamH1 digested pUC18 vector in 20 ul ligation buffer (0.066M Tris pH 7.5, 005M MgCl$_2$, 0.005M Dithiothreitol, 0.001M Adenosine Triphosphate) with 5 units of T4-DNA ligase (PHARMACIA) for 5 hours at room temperature. Competent DH5α cells (prepared by the Hanahan method, Hanahan, *J. Mol. Biol*, 166:557 (1987) were transformed with the ligation mix and spread onto Luria agar plates containing 50 µg/ml ampicillin, 0.001M IPTG (isopropylthio-β-D-galactoside) and 40 µg/ml X-gal (5-bromo-4chloro-3-indoylyl-β-D-galactoside), and the plates were incubated at 37° C. overnight. The white colonies were toothpicked onto fresh Luria agar Ampicillin plates in gridded arrays of 48 per plate, and grown at 37° C. There were 36 arrays picked for a total of ~1700 independent transformants. Each array was then transferred to several nitrocellulose discs on Luria agar Ampicillin plates using a 48 tine prong apparatus and grown overnight at 37° C.

The nitrocellulose discs with the arrays of colonies growing on them were processed for probing by DNA hybridization. Colonies were lysed and DNA denatured by floating the discs on puddles of 0.5M NaOH, 1.5M NaCl for 0.5–1 min followed by neutralization in 1.5M NaCl, 0.5M Tris Cl pH 7.4 for 1–3 min followed by a rinse in 2×SSC. The discs were blotted between sheets of Whatman 3MM paper, then baked at 80° C. for 2 hours. Discs were then stored at room temperature until probed.

2. SCREENING THE pUC18 LIBRARY FOR THE PROTEIN C GENE

A $^{32}$P labelled hybridization probe was made from the *M. hyopneumoniae* DNA insert in the R69 clone. The source of this insert was the clone pSEV6::R69, which was constructed by "cassette" subcloning of the insert in λgtll-R69 into pSEV6, as described in Example II-B. The 0.6 kb insert fragment was generated by digesting the pSEV6::R69 plasmid DNA with the restriction endonuclease EcoR1, releasing the insert, followed by separation by agarose gel electrophoresis (0.7% agarose, TAE buffer, with gel and buffer containing 0.5 μg/ml Ethidium Bromide, 30 V, 3 h). The insert band was visualized under long wave UV light, a slit was made with a scalpel blade just below the desired band and a small piece of Whatman NA50 paper was inserted into the slit below the band. With further electrophoresis the insert fragment migrated onto and bound to the NA50 paper, which was removed and washed in NET buffer (20 mM Tris pH 8, 0.1 mM EDTA). The fragment was eluted from the paper in NET buffer containing 1.0M NaCl, extracted with butanol, precipitated in ethanol, and finally resuspended in TE buffer. The purified fragment was labelled by nick translation with $^{32}$P-α dC using a BIORAD nick translation kit, following the instructions for that kit. The labelled fragment was separated from the unincorporated nucleotides by gel filtration using BIORAD P30 resin in TE buffer.

The hybridization mix contained 50% formamide, 5X SSPE, 1% SDS, 0.1% Sodium Pyrophosphate, 0.15 mg/ml tRNA, 0.0125 mg/ml sonicated salmon sperm DNA. To this was added 400,000 dpm/ml of the labeled probe, after it was denatured by incubation in a boiling water bath for 5 minutes, then chilled. All 36 of the gridded arrays were probed with this mix. Hybridization was carried out in a shaking incubator at 42° C. for 16 hours. The filter discs were then washed 4×15 min in 0.1×SSPE, 1% SDS at 65° C., blotted dry and autoradiographed on KODAK XAR-5 X-ray film at −70° C. using a DUPONT CRONEX LIGHTNING PLUS INTENSIFYING SCREEN. The positions with positive dark signals were marked on the film and the corresponding clones picked from the master plates, streaked out for single colonies, and three such colonies for each positive clone were retested by the same filter hybridization process described above. After rescreening, several purified positive clones (pUC18::6E6, pUC18::9 B1, pUC18::30C6, pUC18::19A3, pUC18::16H2, pUC18::28C2) were grown in liquid culture (Luria broth with 50 μg/ml ampicillin) and DNA isolated using a miniprep method (Holmes & Quigley, *Anal. Biochem.*, 144:193 (1981)). Restriction maps of these clones were made and compared with each other and aligned to determine the overlap between the clones. Also the gels used for this restriction analysis were blotted to nitrocellulose and probed with the R69 insert probe using the Southern blot procedure (Southern, *J. Mol. Biol.*, 98:503 (1975)), in order to determine the position of the R69 probe segment on the large pUC18 clones. One of these clones, pUC18:28C2, was determined to carry the entire gene for the 85 kd protein because it contained more than 2.5 kilobases of DNA on either side of the R69 probe segment (the entire gene should be encoded by <2.4 kilobases). See FIG. 9 for a map of this clone. Clone pUC18::28C2 was used as a source of subclones for sequencing the gene and for site specific in vitro mutagenesis to alter specific nucleotides.

B. DNA SEQUENCING OF GENE FOR PROTEIN C

Figure 9:
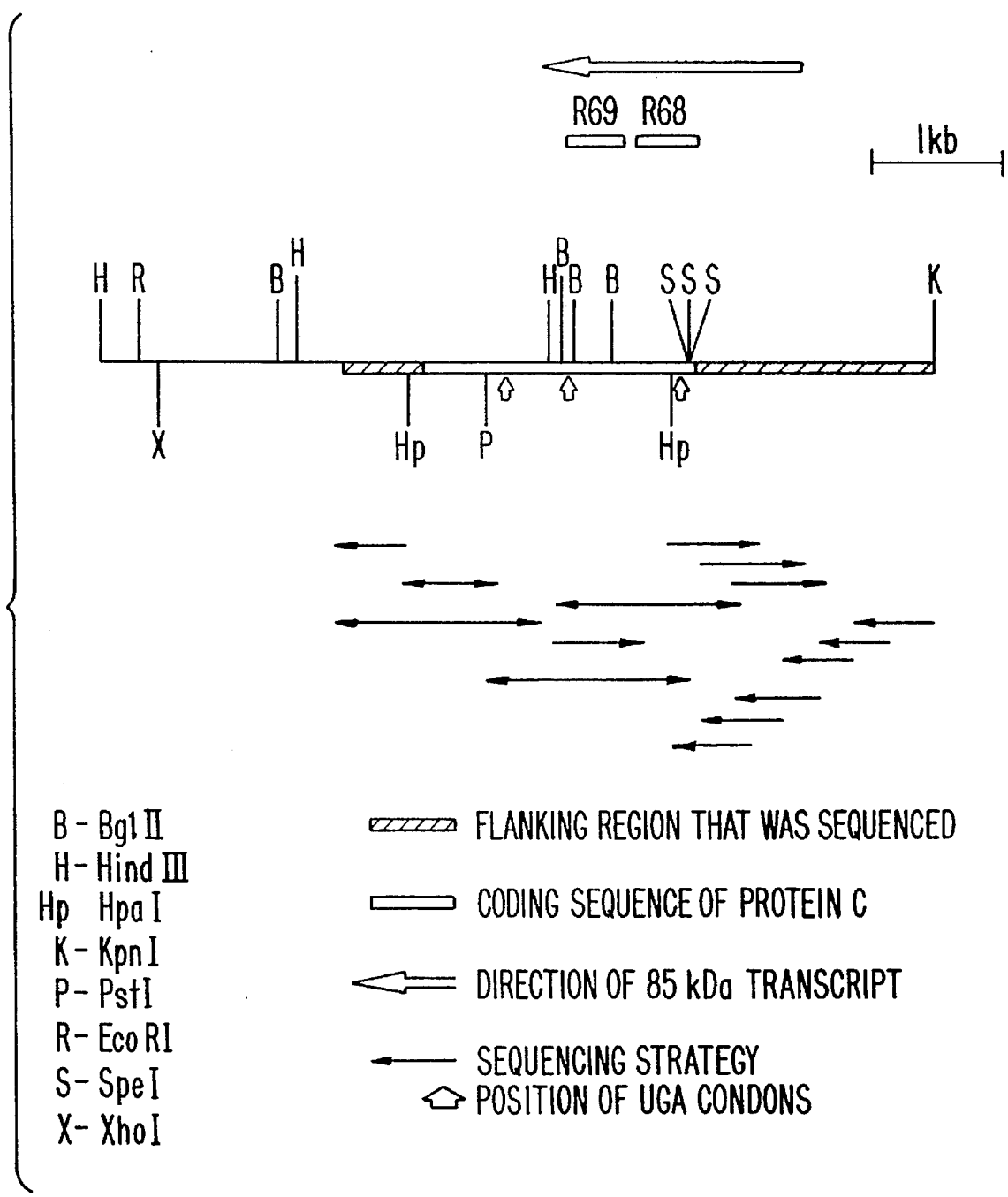

Approximately 4500 base pairs of the genomic clone, pUC18::28C2, sufficient to span the entire gene for Protein C, was sequenced. The sequencing strategies is shown in FIG. 9. Different appropriate restriction fragments from pUC18::28C2 (e.g. KpnI/HpaI, HpaI/HpaI, HpaI/HindIII, HpaI/PstI, HindIII/HindIII, HpaI/BglII, HindIII/PstI etc.) were subcloned into the M13mp18 or M13mp19 phage vectors (Messing et al., *Gene*, 26:101–106, 1983) and sequenced using the enzyme sequenase, specifically engineered for chain-termination DNA sequencing by the procedure of Tabor and Richardson (Tabor et al., *PNAS* 84:4767–4771, (1987)). DNA sequenase sequencing kits were purchased from United States Biochemical Corp. and the reactions were performed according to the manufacturer's instructions. Reactions were analyzed on 6% acrylamide buffer gradient gels (Biggin et al., *PNAS*, 80:3963–3965, (1983)). DNA sequences were analyzed using the Pustell and Kafatos (Pustell et al., *Nucleic Acid Res.*, 12:643–655, (1984)) algorithms obtained as software provided by INTERNATIONAL BIOTECHNOLOGIES INC. (New Haven, Conn.). DNA sequence for the coding region of the gene for Protein C was obtained for both strands of the DNA. Primers used for the DNA sequencing reactions were either the M13 universal primer or synthetic oligonucleotides designed from sequences obtained using the APPLIED BIOSYSTEM DNA Sequencer.

C. AMINO TERMINAL SEQUENCING OF NATURAL PROTEIN C

The gel purified Protein C in NH$_4$HCO$_3$ buffer (See Example X-B below) was applied directly to a glass fiber filter and dried under a stream of argon gas to remove the NH$_4$HCO$_3$. The sequencer with this sample was precycled and then sequenced. The amino-terminal sequence obtained was QQQEANSTNSSP, which matched the translated DNA sequence beginning at nucleotide 1801 of the pUC18::28C2 insert, defining the 5' end of the gene.

D. AMINO ACID SEQUENCING OF PEPTIDES FROM PROTEIN C

1. GENERAL STRATEGY

Since much of the DNA sequence of the 85 kd gene was already known (See Example VIII-B), obtaining the entire amino acid sequence was not necessary. However, it was necessary to obtain enough amino acid sequence to be able to determine the proper reading frame of the DNA sequence, in order to facilitate locating the positions of inframe UGA codons in the coding sequence.

2. PURIFICATION OF PROTEIN C FOR AMINO ACID SEQUENCING

Highly purified Protein C was obtained using a combination of ion exchange column purification followed by preparative gel purification by SDS-PAGE. Starting with the 7S extract (See Example X-A3), the Protein C was partially purified using a Pharmacia Mono Q ion exchange column using the CHAPS method described in Example X-B2. The column fractions enriched for the Protein C were pooled. Preparative gel purification was performed essentially as described in Example X-B4, except that the sample was reduced with 2.5% 2-mercaptoethanol before loading onto the gel. The protein used for endoprotease digestions was eluted from the gel slices in 0.5×running buffer (0.0125M Tris, 0.096M glycine, 0.05% SDS), as described in Example X-B4. For direct amino terminal sequencing (see Example VIII-C), the gel slices were soaked in 0.05M $NH_4HCO_3$, 0.1% SDS, then placed in ISCO sample concentrator cups and eluted in the same buffer at 50 V for 5 hours. The concentrated sample was then diluted 50 fold in 0.01 M $NH_4HCO_3$, 0.05% SDS and then reconcentrated in ISCO sample concentrator cups in the same buffer (50 V, 5 hours).

3. GENERATION AND PURIFICATION OF PEPTIDE FRAGMENTS

For cleavage at lysine, the protein was digested with 2% (w/w) endoproteinase Lys-C (BOEHRINGER-MANNHEIM) in 0.1M Tris, pH 8.6, at 37° C. for 15 h. The protein was also digested with 2% (w/w) Chymotrypsin (BOEHRINGER-MANNHEIM) in 0.25M Ammonium Bicarbonate buffer, pH 7.8, for 4 h at 37° C. The peptides generated were purified by reverse phase HPLC on a 5 μm Vydac C4 (4.5×250 mm) column (The Separations Group) in 0.1% TFA in water with a 0→50% acetonitrile gradient (0.5% per minute). Isolated peptides were applied to a glass fiber filter and sequenced.

4. SEQUENCING OF PEPTIDE FRAGMENTS

Automated sequence analyses were performed on APPLIED BIOSYSTEM 477A pulsed liquid-phase and APPLIED BIOSYSTEM 470A gas-phase sequences equipped with on-line 120A phenylthiohydantoin amino acid analyzers using standard program parameters and analyzer solvents. Sequence analyses were carried out on 30–100 pmol of sample, and repetitive yields of 91–95% were obtained.

E. UGA ENCODES TRYPTOPHAN IN *M. HYOPNEUMONIAE*

The Protein C peptide YLKQNEWD contains a tryptophan (W) in the seventh position which aligns with a TGA codon in the DNA sequence (See FIG. 4, page 3, nucleotides #1411–1413). This proves that TGA (UGA in the RNA) encodes tryptophan in *M. hyopneumoniae* as has been shown in other mycoplasma species.

IX. CONSTRUCTION OF EXPRESSION CLONES TO PRODUCE RECOMBINANT PROTEIN C (TRUNCATED AND FULL LENGTH VERSIONS)

To express Protein C in *E. coli,* it was necessary to mutagenize the UGA codons in the Protein C gene to UGG (the *E. coli* tryptophan codon) and to reconstruct the 5' end of the gene to facilitate insertion into the expression vector. The expression construct pT5T::M851 which encodes the truncated version of Protein C was made first. This construct contains the first two UGA codons which were mutagenized to UGG. Later a DNA fragment containing the C-terminal region of the gene and the third UGA (mutagenized to UGG) was ligated onto this construct to obtain pT5T::M852, which encodes the full length recombinant Protein C. Below is a detailed explanation of how this was accomplished.

A. OLIGONUCLEOTIDE-DIRECTED SITE-SPECIFIC IN-VITRO MUTAGENESIS TO CHANGE UGA TO UGG CODONS USING GENETIC SELECTION

Oligonucleotide-directed site-specific in vitro mutagenesis was carried out to change the UGA to UGG codons. Mutagenesis was carried out using the MUTA-GENE IN VITRO MUTAGENESIS KIT from BIORAD based on a method described by Kunkel (Kunkel et al., *Methods Enzymol.,* 154:367–382 (1987)). The host cell used for genetic selection for mutagenesis is the *E. coli* strain CJ236 (Genotype:dut, ung, thi, rel A1, pCJ105[cap$^r$]) which provides a very strong selection against the non-mutagenized strand of a double-stranded DNA due to the dut (dUTPase) and ung (uracil N-glycosylase) mutations. Template DNA, substituted with uracil and used for mutagenesis, is selectively destroyed when transformed into host cells that contain wild-type ung loci, such as JM103 in this case, thus allowing preferential replication of the newly synthesized mutated DNA.

Mutagenesis of the three UGA codons was carried out in two parts. The first part involved the simultaneous changing of the A to G in the first two UGA codons (nucleotide positions 231 and 1068) contained in the DNA fragment from the beginning of the gene for Protein C to the HindIII recognition site at nucleotide #1294. The second part involved the changing of nucleotide A to G in the third UGA codon at nucleotide position 1413.

To perform mutagenesis on the first two UGA codons described above, clone pSEV6::R68SKH was used. pSEV6::R68SKH was obtained by joining the ~2.1 kb HpaI fragment from the genomic clone pUC18::28C2 (see FIG. 9) to the HpaI site in pSEV6::R68. The expression clone pSEV6::R68 is a β-galactosidase fusion clone which encodes part of Protein C. It was derived from the λgtll clone, R68, by "cassette" subcloning into the plasmid pSEV6 (See Example III-B). The insert in R68 begins before the 5' end of the Protein C coding sequence (as defined by the amino-terminus of the protein), but is in frame with the protein coding sequence, making a fusion protein which is partially Protein C and partially from the region upstream of the Protein C coding sequence.

The resulting ~2.4 kb SstI/HindIII fragment containing the 5'-end to the above-mentioned HindIII site of the gene for Protein C was subcloned into M13mp18 to obtain single-stranded DNA template for mutagenesis. Two oligonucleotides were designed to simultaneously change the two UGA codons to UGG's in one mutagenesis experiment. The oligonucleotide 5' GGGAAATTTTGTTTTCCAACCAAGCATCTAAAAGTGCCTCG 3' was used to substitute the A at nucleotide position 231 (FIG. 4) and the oligonucleotide 5' GATCTTCGTCTTGGAGTTGACTCAACTTGCAAAATTTAATC 3' was used to substitute the A at nucleotide position 1068 (FIG. 4). These two oligonucleotides are the complement of the coding strand shown in FIG. 4 (and also read in the opposite orientation). The crucial substituted nucleotide in the oligonucleotide is underlined.

One of five clones picked and sequenced (clone S9e) in the mutagenesis experiment was confirmed to have both of the UGAs changed to UGG's. The correctly mutagenized SstI/HindIII fragment was subcloned back into the original vector, pSEV6:R68SKH, and the mutagenized clone was designated as pSEV6:R68SKHM. The mutagenesis was also confirmed by increase in size of the β-galactosidase fusion protein, expected for replacing the *E. coli* termination codons (UGA) with tryptophan (UGG) codons.

To mutagenize the A to G in the third UGA codon at nucleotide position 1413 (FIG. 4), the oligonucleotide 5' CTATCTAAAACAAAATGAATGGAT-CAAGTTAAAACAACAAATAATGGCC 3' was used. This oligonucleotide reads the same as the coding strand (except for the A–G substitution) because the single strand clone used to do the mutagenesis was the opposite strand.

To mutagenize this third UGA to UGG, the ˜2 kb HindIII fragment from pUC18::28C2 (see FIG. 9) was cloned into M13mp19 and mutagenesis was carried out using the MutaGene kit according to manufacturer's specifications. Nine of 10 clones sequenced were confirmed to have the A changed to G and clone 2Ha was used for the remaining experiments. The HindIII fragment from clone 2Ha was ligated into HindIII cut and dephosphorylated pSEV6::R68SKHM. The resulting plasmid, designated pSEV6::M852a-1, contains the entire gene for Protein C with the three UGA codons having been changed to UGG's. The mutagenesis was again confirmed by further increase in size of the β-galactosidase fusion protein.

B. RECONSTRUCTION OF 5'-END OF THE GENE FOR PROTEIN C

Using the mutagenized clone pSEV6::R68SKHM, the 5'-end of the gene for Protein C was reconstructed for expression of a nonfused version in E. coli. Restriction enzyme search of the DNA sequence of Protein C gene showed that there are three SpeI sites within the first 120 nucleotides at the 5'-end of the gene (see FIG. 9). Oligonucleotides were designed to rebuild the amino-terminus of the gene, taking advantage of the third SpeI site to join the oligonucleotides to the remaining part of the gene. In designing the oligonucleotides, the Mycoplasma codons were changed to *E. coli*-preferred codons, the first two SpeI sites were eliminated, and an EcoRI and a NheI restriction sites were engineered in, all without changing the original amino acid sequence of the Protein C. The four oligonucleotides used were:
1) oligonucleotide NA: 5'GATCCGATCTTGGAGGAT-GATTAAATGCAGCAGCAGGAAG-CAAACTCCACGAATTCTAGCCCGAC 3'
2) Oligonucleotide NB: 5'TCGGGCTAGTCGGGCTA-GAATTCGTGGAGTTTGCTTCCTGCTGCT-GCATTTAATCATCCTCCAAGATCG 3'
3) Oligonucleotide NC: 5'TAGCCCGAGCCCGAGC-CCGACTAGCCCGAGCCCGGCTAGC-CCGAGCTCCAGCCCGAGCCCGA 3'
4) Oligonucleotide ND: 5'CTAGTCGGGCTCGGGCTG-GAGCTCGGGCTAGC-CGGGCTCGGGCTAGTCGGGCTCGGGC 3'

Oligonucleotides NA and NB are complementary to each other and oligonucleotides NC and ND are complementary to each other. To rebuild the 5'-end of the gene for Protein C, the four oligonucleotides were kinased, NA and NB were annealed to each other and NC and ND were annealed to each other. pSEV6::M851 was digested with SpeI and the digested DNA was ligated to annealed oligos NC and ND. This DNA was then ligated to annealed NA and NB oligos to complete the reconstruction of the 5'-end of the gene. The ligated DNA mix was digested with BamHI and HindIII to obtain the DNA fragment containing the 5'-end of the gene to the HindIII recognition sequence at nucleotide position 1294. This DNA fragment was used for expression of the truncated form of Protein C described below. The reconstructed region of 5'-end is shown in FIG. 5.

C. RECOMBINANT EXPRESSION OF PROTEIN C USING AN EXPRESSION VECTOR BASED ON THE "T7" PROMOTER SYSTEM (VECTOR pT5T)

1. DESCRIPTION OF pT5T

The T7 promoter based expression vector pT5T is essentially the same as pJU1003 (Squires, et al., *J. Biol. Chem.*, 263:16297–16302 (1988)), except that there is a short stretch of DNA between the unique BglII site 5' to the T7 promoter and the ClaI site in the tetracycline resistance gene. The sequence of this DNA is: ATCGATGATA AGCTGT-CAAA CATGAGAATT GAGCTCCCCG GAGATCCTTA GCGAAAGCTA ClaI

AGGATTTTTT TTAGATCT

BglII

2. CONSTRUCTION OF THE EXPRESSION VECTOR FOR THE TRUNCATED PROTEIN C

The vector pT5T was linearized with BamHI and HindIII restriction enzymes and gel-purified. The DNA fragment, from the rebuilt 5'-end of the protein C gene, to the HindIII site at nucleotide position 1294 excised from clone pSEV6::R68SKHM (See Example IX-A1) with BamHI and HindIII containing the first two mutagenized UGA codons, was ligated to form the expression construction pT5T::M851.

3. CONSTRUCTION OF THE EXPRESSION VECTOR FOR THE FULL-LENGTH PROTEIN C

Figure 10:
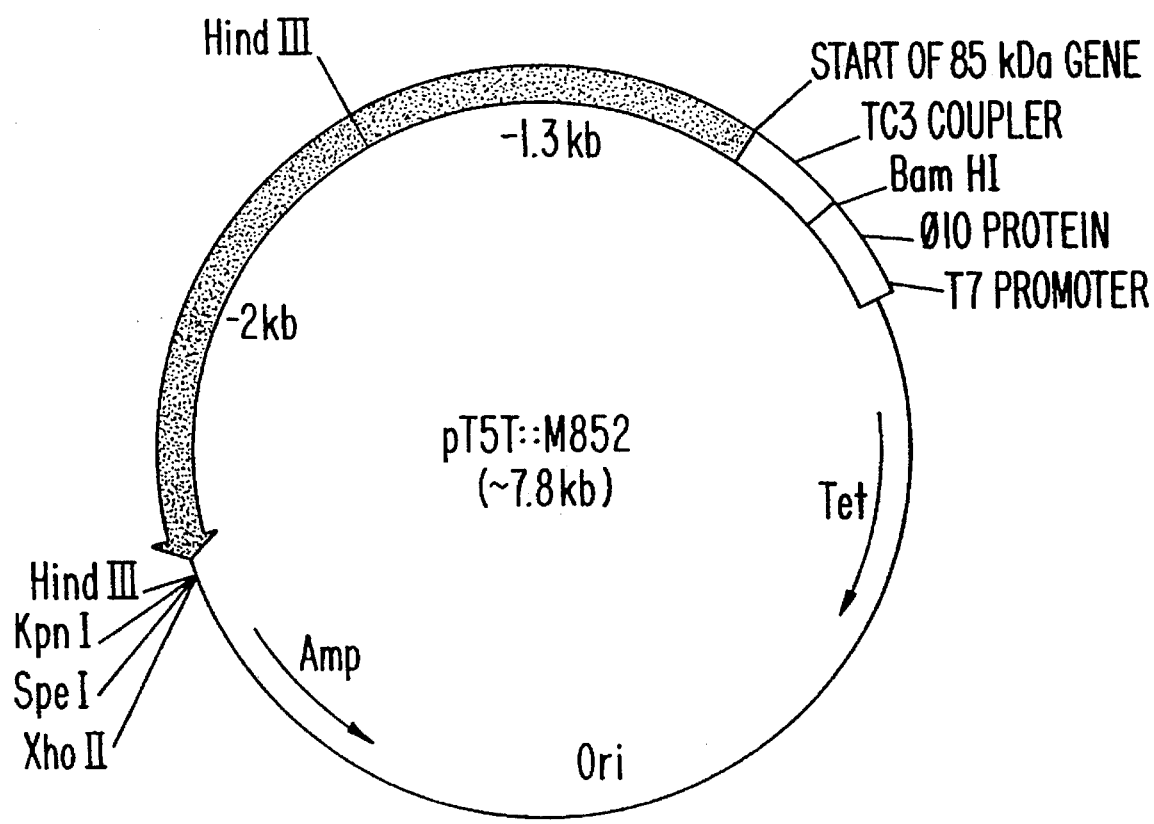

For expression of the entire Protein C protein, the ˜2 kb HindIII gel-purified fragment (excised from clone 2Ha, see Example IX-A), containing the third mutagenized UGA codon and the C-terminus of the gene, was ligated to pT5T::M851 (digested with HindIII restriction enzyme and treated with alkaline phosphatase to dephosphorylate the vector to minimize self-ligation of the vector). Because the HindIII fragment could ligate to the digested vector in either orientation, transformants were restriction site mapped to ascertain the correct orientation of the HindIII fragment. This resulted in a construct designated pT5T::M852, which is illustrated in FIG. 10.

4. EXPRESSION OF RECOMBINANT PROTEIN C (BOTH TRUNCATED PROTEIN C AND THE FULL-LENGTH PROTEIN C)

Both pT5T::M851 (truncated Protein C) and pT5T::M852 (full-length) were transformed into the *E. coli* strain BL21/DE3 for expression. This strain (described in Studier and Moffat, *J. Mol. Biol.*, 189:113–130 (1986)) contains the T7 RNA polymerase gene under control of the IPTG inducible lac promoter on a non-excisable lysogenic λ bacteriophage.

The clone found to be expressing an IPTG-inducible protein migrated at a molecular weight of ~50 kd (Truncated Protein C) by pT5T::M851 is designated pT5T::M851-B2B, and the clone found to be expressing an IPTG-inducible protein migrating at a molecular weight of ~85 kd (full length Protein C) by pT5T::M852 is designated pT5T::M852-1. pT5T::M852-1 produces a recombinant protein which co-migrates on SDS polyacrylamide gels with natural 85 kd protein isolated from mycoplasma. Both the short 85 kd and the full-length 85 kd recombinant proteins are immuno-reactive with sera from pigs immunized with gel-purified natural 85 kd protein on Western blots (See Example X-J).

DNA sequencing of pT5T::M851 and pT5T::M852 confirmed that the sequences of the recombinants were correct. Amino terminal amino acid sequencing of the intact recombinant full length Protein C yielded the sequence MQQQEANSTNSSPT confirming the correct initial sequence with a methionine added to the amino terminus (See FIG. 4). To determine this sequence, a sample of the insoluble pellet following French Press disruption of the cells (See Example X-C.) was solubilized in sample buffer and electrophoresed on a polyacrylamide gel using the MZE system 3328.IV, described by Moos et al. (*J. Biol. Chem.*, 263:6005–6008 (1988)). Separated proteins were transblotted to a PVDF Immobilon membrane and visualized by Coomassie staining. The region containing the recombinant Protein C band was cut out of the membrane, destained, inserted into the sequencer, and sequenced (See Example VIII-D4).

Expression and purification of full length and truncated recombinant Protein C are described in Example X-C and X-D respectively.

X. VACCINATION EXPERIMENTS

A. PROTEIN EXTRACTS FROM MYCOPLASMA CELLS USED AS VACCINES

1. GROWTH AND HARVEST OF *M. HYOPNEUMONIAE* CELLS

*M. hyopneumoniae* strain 64C was grown in Friis medium (Friis, *Nord. Veterinaer Med.*, 27:337–339, (1975)) at 37° C. in shaker flasks (1200 ml in 2l flask) at 230 rpm. Cells were grown to $OD_{650}$=0.2–0.3 which took 2.5–3 days and was accompanied by a shift in color of the medium from red to yellow/orange and visible turbidity of the culture. Cells were harvested by centrifugation at 16,000×g for 15 minutes at 4° C. Cells were resuspended in 1/10 volume 0.25M NaCl and then centrifuged again under the same conditions. The final cell pellet was resuspended in 1/50 volume 0.25M NaCl at $OD_{650}$=10.

2. LOW pH (S1) EXTRACTION OF PROTEINS FROM *M. HYOPNEUMONIAE* CELLS

To *M. hyopneumoniae* cells harvested and resuspended as described above in Example X-A1, ¼ volume of 10 mM glycine, pH 2.0 was added and mixed with the cells by rocking for 15 minutes at 4° C. The final pH of the mix was 2.5. The mix was then centrifuged at 48,000×g for 15 minutes at 4° C. The supernatant was removed and was called the S1 extract. The S1 extract contains a variety of proteins depicted in the photograph of a SDS-polyacrylamide gel in FIG. 8. The major protein components are 87 kd, 85 kd (Protein C), 65 kd, 50 kd, as well as several other minor proteins. The S1 extract was concentrated and desalted using an AMICON ultrafiltration cell (stirred cell type) fitted with an AMICON YM30 DIAFLO ULTRAFILTRATION membrane operated at 40 psi at 4° C. Initial concentration of the extract to 1/100 of the starting volume took several hours and left a thick protein coating on the filtration membrane. When ½ the starting volume of 2 mM glycine pH 2.5 was added to the vessel and stirred, the protein coating released from the membrane in sheets which dissolved in the 2 mM glycine. After redissolving, the second concentration step to 1/100 of the starting volume proceeded rapidly at 40 psi, usually taking <1 hour. This concentrate was removed from the vessel and the membrane washed 2× with 2–3 ml of 2 mM glycine pH 2.5 and the washes were pooled with the concentrate resulting in a desalted concentrate that was about 1/50 the original volume. This concentrated S1 extract, called S1c, was indistinguishable from the S1 extract in its protein composition, as judged by the protein bands on Coomassie blue stained SDS polyacrylamide gels.

3. FRACTIONATION OF PROTEINS BY PH PRECIPITATION

When the pH of the concentrated, desalted S1c was raised to pH 7.0 by the addition of 1M MOPS (3-[N-Morpholio] propanesulfonic acid) pH 7 to 40 mM, a fine white precipitate formed. This precipitate was removed by centrifugation (15 min, 48,000×g, 4° C.) and then redissolved in 2 mM glycine pH 2.5. The supernatant, called 7S, contained about 40% of the total protein and was enriched for the 85 kd and 65 kd proteins with about half of the 50 kd protein and several minor proteins as well. The redissolved pellet, called 7P, contained the remaining 60% of the protein and was enriched for the 87 kd protein with half of the 50 kd protein and several minor proteins. Neither fraction was completely free of proteins contained in the other fraction. The proteins in each fraction are depicted in the Coomassie stained gel in FIG. 8.

B. PURIFICATION OF PROTEIN C FROM *M. HYOPNEUMONIAE* CELLS

1. ION EXCHANGE CHROMATOGRAPHY

The natural Protein C was purified by ion exchange chromatography using two different methods: 1) the CHAPS method utilized a buffer containing the zwitterionic detergent CHAPS and the 7S extract as the starting material; and 2) the Urea method utilized a buffer containing 6M Urea and the S1c extract as the starting material. Purification using either of these agents was adequate, though the urea containing buffer gave somewhat better resolution in elution profiles. Without any detergent or denaturant, resolution of elution peaks was extremely poor.

2. CHAPS METHOD

The starting material for purification of the natural Protein C was the extract known as 7S—the pH 7 supernatant derived from the concentrated low pH extract—S1 (see descriptions of extracts, Example X-A. The 7S is enriched for the 85 kd protein (Protein C) as well as a 65 kd protein and a 50 kd protein and also contains other minor contaminants.

Ion exchange chromatography was performed using a PHARMACIA Mono Q HR5/5 column (1 ml bed volume) connected to a PHARMACIA FPLC system. The CHAPS buffer consisted of 0.05% CHAPS (3-[(3-Cholamidopropy- 1)dimethylammonio] -1-propanesulfonate), 0.02M BISTRIS (bis[2-Hydroxyethyl]iminotris-[hydroxymethyl]methane), pH 6.0. A typical sample consisted of 34 ml 7S extract, 3.05 ml H20, 0.76 ml 1M BIS-TRIS pH 6.0, 0.19 ml 10% CHAPS, for a total of 38 ml with 0.02M BIS-TRIS pH 6, 0.05% CHAPS. This sample was filtered through a GELMAN ACRODISC disposable filter assembly with a 0.2 μm pore size. The sample was loaded onto the column at 1 ml/min, the column was washed with 5–10 column volumes of CHAPS buffer, then eluted with a linear gradient of NaCl in the same buffer. The gradient ran from 0 to 0.25 m NaCl over a volume of 40 ml. The 85 kd protein eluted at 0.08–0.10M NaCl with some trailing of the peak into the higher [NaCl] fractions. Samples from selected fractions were analyzed by SDS-PAGE and the gels were silver stained to reveal those fractions containing the 85 kd protein. The fractions which were enriched for the 85 kd protein were pooled. These pools contained >60% 85 kd protein and the rest a variety of contaminating proteins, as estimated visually by Coomassie stained gels. Protein concentrations were determined using a BIORAD Protein Assay kit.

3. UREA METHOD

The urea buffer consisted of 6M urea (BRL, Ultrapure, Enzyme grade) in 0.02M BIS-TRIS pH 6.0. The starting material was the concentrated low pH extract—the S1c. A typical sample contained 4 ml S1c, 3.8 ml $H_2O$, in which was dissolved 3.85 g Urea. After the Urea was dissolved, 0.2 ml 1M BIS-TRIS pH 6.0 was added, yielding ~10 ml of solution containing 6M Urea, 0.02M BIS-TRIS pH 6.0. This sample was filtered through a GELMAN ACRODISC disposable filter assembly with a 0.2 μm pore size. The sample was loaded onto the Pharmacia Mono Q HR 5/5 column at 1 ml/min, the column was washed with 5–10 column volumes of Urea buffer, then eluted with a linear gradient of NaCl in the same buffer. The gradient ran from 0 to 0.25M NaCl over a volume of 40 ml. The 85 kd protein eluted at 0.04–0.08M NaCl in fairly sharp peaks without much trailing into higher fractions. Samples from selected fractions were analyzed by SDS-PAGE and the gels were silver stained to reveal those fractions containing the 85 kd protein. The fractions which were enriched for the 85 kd protein were pooled. These pools contained 50% 85 kd protein with a major contaminant at ~50 kd and a variety of minor contaminating proteins, as estimated visually by Coomassie stained gels. Protein concentrations were determined using a BIORAD Protein Assay Kit.

4. GEL PURIFICATION

Further purification of the 85 kd protein was accomplished by preparative SDS polyacrylamide gel electrophoresis (SDS-PAGE). The resolving gel was 8 cm long by 14 cm wide by 3 mm thick and was 7.5% acrylamide (7.3% acrylamide: 0.2% N,N'-Methylene-bis-acrylamide) in 0.1% SDS, 0.375M Tris-HCl pH 8.8. The stacking gel was 1 cm long with the same width and thickness as the resolving gel and was 4.5% acrylamide (4.38% acrylamide:0.12% N,N'-Methylene-bis-acrylamide) in 0.1% SDS, 0.125M Tris HCl pH 6.8. The Running buffer contained 0.025M Tris base, 0.192M glycine, 0.1% SDS, pH 8.3. The sample buffer contained 10% w/v glycerol, 3% SDS, 0.0625M Tris-HCl pH 6.8. No reducing agent or dye was used for these samples. The sample (pooled column fractions enriched for the 85 kd protein) was mixed with an equal volume of sample buffer and heated in a boiling water bath for 10 min, then cooled to room temperature. Five ml of this mix was loaded into the gel apparatus and electrophoresed at 50 mA until the ion front reached the bottom of the gel (~2.5 hours).

To determine the location of the protein band in the gel a special blotting procedure was used. When the gel was finished running, it was removed from the electrophoresis apparatus and laid horizontally on a glass plate, and the stacking gel removed by cutting with a razor blade. On the upper exposed surface of the gel was laid a piece of wetted (in $H_2O$) nitrocellulose sheet (Schleicher & Schuell, BA-83, 0.2 μm pore size), cut slightly larger than the gel. Over this was laid a sheet of wetted Whatman 3MM paper, followed by 2 sheets of dry 3MM paper, a glass plate, and a weight (300–500 g). After 30 minutes at room temperature, enough protein was transferred to the nitrocellulose that it could be visualized by staining. Before removal from the surface of the gel, the back of the nitrocellulose sheet was marked with a black VWR lab marker to indicate the position of the edges of the gel, so that the gel could be aligned with the blot after staining. The nitrocellulose was then removed from the gel, washed 3 times in TBS+0.3% Nonidet P-40 (TBS=Tris-Buffered Saline=0.15M NaCl, 0.1M Tris-HCl pH 8.0). Then the sheet was stained in the same solution to which had been added 0.1% Waterproof Black India Ink (Koh-i-noor Rapidograph 3080-F Universal). After 10–15 minutes of shaking in the stain solution at room temperature, stained bands appeared on the side of the nitrocellulose sheet which had been in contact with the gel. The gel was then aligned with the marks on the nitrocellulose and the area over the darkest and thickest staining band was excised from the gel using a razor blade. To facilitate removal of protein from the gel slice, the slice was crushed by forcing it through a disposable plastic syringe with no needle attached into a tube containing 0.5X Running Buffer (see above). The crushed gel slices were stored in this buffer at 4° C.

Elution of the protein from the gel slices was accomplished using ISCO sample concentrator cups. The crushed gel slices were placed in the cups in 0.5X Running Buffer and electroeluted at 1 Watt per cup for 3–4 hours. The concentrated sample was removed using a pipetman and pooled with samples from other cups. The concentration of protein in these samples was estimated by running different amounts of the sample along side different amounts of a known standard on SDS-PAGE and comparing the intensity of Coomassie Blue staining of the protein bands.

The concentrated samples were pooled, diluted to a concentration of 1.0 mg/ml with 0.5 X Running Buffer, and stored at 4° C. until used for vaccine testing.

C. EXPRESSION AND PURIFICATION OF FULL LENGTH RECOMBINANT PROTEIN C.

Strain pT5T::M852-1 (See EXAMPLE IX-C) was grown in shaker flasks (350 ml in 21 baffled flasks, 250–350 rpm, 37° C.). The Medium used was Luria Broth (1% tryptone, 0.5% Yeast extract, 1% NaCl, pH 7.5) with 10 μg/ml tetracycline. Cells were induced at $OD_{600}$=0.7–0.9 with 0.4 mM IPTG (isopropyl-thiogalactopyranoside). Cells were harvested 8–11 hours after induction ($OD_{600}$=1.4–1.6) by centrifugation 9000×g, 10 min, 4° C. Cells were resuspended in 1/10 volume 20 mM Tris pH 8.2, repelleted at 9000×g for 10 min, and finally resuspended in 1/100 volume of the same buffer. Cells were disrupted using a French Pressure cell (3 passages, 18,000 psi). The whole cell lysate was centrifuged at 48,000×g for 30 min at 4° C. More than 90% of the full length recombinant protein C was contained in the pellet after this centrifugation. This pellet was resuspended in the same value of 20 mM Tris pH 8.2 as a milky white suspension. The protein was solubilized by mixing 1:1 with gel sample buffer (100° C., 10 min) and purified by preparative polyacrylamide gel electrophoresis as described for the natural Protein C purified from *M. hyopneumoniae* cells (See GEL PURIFICATION; Example X-B).

D. EXPRESSION AND PURIFICATION OF TRUNCATED PROTEIN C.

Strain pT5T::M851-B2B (See EXAMPLE IX-C) was grown in shaker flasks (350 ml in 21 baffled flasks, 250–350 rpm, 37° C.). The medium used was Luria Broth (1% tryptone, 0.5% Yeast extract, 1% NaCl, pH 7.5) with 10 μg/ml tetracycline. Cells were induced at $OD_{600}$=0.7–0.9 with 0.4 mM IPTG (isopropyl thiogalactopyranoside). Cells were harvested 3–4 hours after induction ($OD_{600}$=1.4–1.6) by centrifugation (9000×g, 10 min, 4° C.). Cells were resuspended in 1/10 volume 20 mM Tris pH 8.2, repelleted at 9000×g for 10 min, and finally resuspended in 1/100 volume of the same buffer. Cells were disrupted using a French Pressure cell (3 passages, 18,00 psi). The whole cell lysate was centrifuged at 48,000×g for 30 min at 4° C. More than 90% of the truncated recombinant protein C remained in the supernatant after this centrifugation. Two methods were used for purification of the truncated recombinant Protein C. For ion exchange chromatography, the supernatant was diluted 5–10 fold in 20 mM Tris pH 8.2 and urea was added to 6M. This was then passed over a MonoQ FPLC column and eluted with an NaCl gradient essentially as described in the Urea method of ion exchange chromatography purification of the natural Protein C (See Example X-B) except that the buffer used contained 20 mM Tris pH 8.2. Truncated Protein C eluted at 0.10–0.12M NaCl in the NaCl gradient.

Truncated Protein C was also purified by preparative gel electrophoresis. The supernatant was mixed 1:1 with gel sample buffer and purified by preparative polyacrylamide gel electrophoresis as described for the natural Protein C purified from *M. hyopneumoniae* cells (See GEL PURIFICATION; Example X-B4).

E. PROTOCOL FOR VACCINATION EXPERIMENTS

Healthy, 6-week-old conventional pigs were purchased and assigned to pens of 5–6 pigs each. Pigs in 3 pens (a total of 15–18 pigs per group) were vaccinated by intramuscular injection with 3.0 ml/pig of experimental vaccine or a placebo, in a water-in-oil emulsion adjuvant. Pigs received 4 vaccinations (50,100,200, and finally 400 micrograms total protein per injection) at 7 day intervals.

Two days following the final injection, three *Mycoplasma hyopneumoniae* infected donor pigs were placed in each pen to provide a natural source of infection for the vaccinates. The donor pigs were artificially infected with *M. hyponeumoniae* by intranasal infusion of a homogenate made from infected lung tissue, which results in a serious infection. This infection was started at the same time that the vaccinate pigs received their first injection, so that a serious infection was present at the time of mixing. The vaccinates and the donors were kept separated until mixing. Ventilation in the building was reduced to facilitate transmission of the disease. Blood samples were collected from each pig, one prior to the first injection, and one after the last injection but before mixing with the donor pigs.

Six weeks after mixing, each pig was killed and the lungs were examined for severity of the disease. One person, blinded as to the treatment, did all lung evaluations. The primary criterion was the percent of gross pneumonic lesions in the lungs as estimated by visual inspection. Lung tissue was also collected for an Indirect Fluorescent Antibody (IFA) test to determine whether the gross lesions contained *Mycoplasma hyopneumoniae* infections (See Example X-G). These samples were also cultured for aerobic bacteria other than mycoplasma. Animals which had visible gross lesions and tested positive in the IFA test were considered to be infected when determining the incidence of the disease in the different groups. The average lesion score (mean % lesions) was also used as a measure of the effectiveness of a vaccine. For the purpose of averaging, those animals which were scored as having >0% but <1% lesions were given a lesion score of 0.5%. The pneumonic lesion data were statistically analyzed using the square root transformation and the means shown in the Table 2 were transformed to the original scale.

Other tests that were conducted in some cases were:

1. ELISA tests (See Example X-H) and Western blots (See Example X-J) to determine whether sera from vaccinated pigs reacted with specific antigens.

2. Metabolic Inhibition tests (Example X-I) to determine whether sera from vaccinated pigs had any in vivo effects on growth of *M. hyopneumoniae* cells.

3. Histological examination of pneumonic lung tissue (See Example X-K) to determine the severity of lung lesions at the microscopic level.

F. RESULTS OF VACCINATION TRIALS

The results of the vaccination trials are presented in Table 2 below:

TABLE 2

Vaccine Trial Results

| Expt. No. | Vaccine Protein(s) | Gross Penumonic Lesions Incidence | Gross Penumonic Lesions Mean % | IFA Positive |
|---|---|---|---|---|
| 8702 | S1 | 7/15[a] | 0.63[a] | 7/15[a] |
|  | Nonvaccinated | 14/15[b] | 8.11[b] | 14/15[b] |
| 8805 | 7S | 5/15[a] | 0.23 | 5/15[a] |
|  | 7S, 1.25% SDS | 4/15[a] | 0.08[a] | 7/15[b] |
|  | 7S, 6M Urea | 4/14[a] | 0.28 | 6/14[a] |
|  | Nonvaccinated | 12/15[b] | 2.23[b] | 12/15[b] |
| 8802 and 8902 | Protein C (column purified) and Protein C (gel purified) | 15/33[a] | 0.66[a] | 17/32[a] |
|  | Placebo | 27/33[b] | 3.13[b] | 27/32[b] |
| 8904 and 8905 | Full-length Recombinant Protein C | 17/30[a] | 0.44[a] | 17/30[d] |
|  | Truncated Recomb. Protein C | 19/30[a] | 0.86[a] | 19/30[a] |
|  | Placebo | 28/30[b] | 2.90[b] | 28/30[b] |

[a], [b]Values in vertical columns with different superscripts are significantly different, $P \leq .05$.

LEGEND FOR TABLE 2—VACCINE TRIAL RESULTS

The protocol for the vaccine trials is described above in Example X-E.

The pneumonic lesion data were statistically analyzed using the square root transformation and the means shown in the Table 2 were transformed to the original scale.

INCIDENCE: A ratio of the number of pigs in a group which have gross pneumonic lesions and score positive on the IFA test to the total number of pigs in the group. This ratio indicates the degree to which the transmission of the disease is reduced by the vaccination.

MEAN %: The average lesion score of all the pigs in a particular group. This number allows comparison of the severity of the disease between different groups.

IFA POSITIVE: The IFA (Indirect Fluorescent Antibody) test detects the presence of *M. hyopneumoniae* cells in the lung tissue, particularly in the gross lesions. This indicates whether the lesions seen are in fact caused by *M. hyopneumoniae* or some other agent (other mycoplasma species or bacteria). It is expressed as a ratio of the number of pigs in a group scoring positive in the IFA test to the total number of pigs in the group. Detailed description of this test in Example X-G.

General conclusions based of the results obtained are listed below:

1. S1 EXTRACT EXHIBITS SIGNIFICANT PROTECTION AGAINST *M. HYOPNEUMONIAE* INFECTION. In experiment 8702, S1 vaccinates showed significant reduction in incidence, mean percent lesion scores, and numbers of pigs which were IFA positive, when compared to nonvaccinated controls.

2. 7S EXTRACT EXHIBITS SIGNIFICANT PROTECTION AGAINST *M. HYOPNEUMONIAE* INFECTION. In experiment 8805, 7S vaccinates showed significant reduction in incidence, and numbers of pigs which were IFA positive, when compared to nonvaccinated controls. The mean % lesion scores were also reduced for this group but were not statistically significant at $P \leq 0.05$.

3. THE 7S EXTRACT CAN BE DENATURED IN THE DETERGENT SDS OR IN UREA WITHOUT DESTROYING ITS PROTECTIVE PROPERTIES. In experiment 8805, vaccination with 7S which had been denatured in 1.25% SDS resulted in significant reduction in incidence and in mean % lesion scores, compared to the nonvaccinated controls. IFA positive scores were reduced but were not significant at $P \leq 0.05$. Vaccination with 7S which had been denatured in 6M urea resulted in significant reduction in incidence and IFA positive scores when compared to non-vaccinated controls. Mean % lesion scores were reduced but were not significant at $P \leq 0.05$.

4. PROTEIN C (PURIFIED FROM *M. HYOPNEUMONIAE* CELLS) EXHIBITS SIGNIFICANT PROTECTION AGAINST *M. HYOPNEUMONIAE* INFECTION. Results were combined between experiments 8802 (in which protein C was purified by ion exchange chromatography) and 8902 (in which Protein C was further purified by preparative polyacrylamide gel electrophoresis). There was no statistically significant difference between the results of these two tests, so they were combined. Significant reductions in incidence, means % lesions, and IFA positive scores are exhibited compared to placebo vaccinated controls.

5. FULL LENGTH RECOMBINANT PROTEIN C EXHIBITS SIGNIFICANT PROTECTION AGAINST *M. HYOPNEUMONIAE* INFECTION. Results are combined for experiments 8904 and 8905 (separate tests, both with preparative polyacrylamide gel purified protein). Significant reductions in incidence, means % lesion scores, and IFA positive scores were exhibited when compared to placebo vaccinated controls.

6. TRUNCATED RECOMBINANT PROTEIN C EXHIBITS SIGNIFICANT PROTECTION AGAINST *M. HYOPNEUMONIAE* INFECTION. Results are combined for experiments 8904 (in which the protein was purified by ion exchange chromatography) and 8905 (in which the protein was purified by preparative polyacrylamide gel electrophoresis). Significant reductions in incidence, means % lesion scores, and IFA positive scores are exhibited when compared to placebo vaccinated controls.

G. INDIRECT FLUORESCENT ANTIBODY (IFA) TEST

In order to determine whether the lesions observed in infected animals actually were infected with *M. hyopneumoniae*, tissue samples were taken from lesions in infected lungs or from the tips of the lobes of the lungs in animals with no detectable gross lesions. This is the region of the lung where infection is most likely to occur. Frozen sections of these tissues were made, mounted and acetone fixed on glass slides. A rabbit anti-*M. hyopneumonia* serum was bound to the sections, washed, and followed by a Fluorescein-linked goat anti-rabbit IgG. Unbound antibodies were washed off and the sections were observed under a fluorescence microscope. Sections which displayed bright fluorescent rings around the alveoli were scored as positive. Control sera showed only background fluorescence.

H. ENZYME LINKED IMMUNOSORBANT ASSAY (ELISA)

Wells in 96-well microtiter plates were coated with 0.3 μg/well of antigen (purified natural Protein C, recombinant full-length or truncated Protein C, or sonicated whole mycoplasma cells) in 0.045M sodium carbonate buffer pH 9.6. Nonspecific binding of antibodies was blocked with 5% gelatin in PBS (10 mM sodium phosphate, 0.15M NaCl, pH 7.4.). Serial dilutions of primary antibodies (vaccinated pig sera) in PBS+1% gelatin+ 0.05% Tween 20 were bound to the antigen, washed and followed by the secondary antibody peroxidase linked goat anti-swine IgG (KIERKEGARD AND PERRY) in the same buffer. After washing, TMB Microwell Peroxidase Substrate (KIERKEGARD AND PERRY) was added, the reaction run for 2–5 min at room temperature and terminated by addition of an equal volume of 1M $H_3PO_4$. Colored reaction products were read at 450 nm and recorded.

Results indicated that sera from pigs vaccinated with natural Protein C had strong reactivity towards both of the recombinant proteins when compared with placebo vaccinated controls. Conversely, sera from pigs vaccinated with either recombinant protein reacted strongly with the natural Protein C in the wells. Sera from pigs vaccinated with natural or recombinant Protein C reacted strongly to sonicated *M. hyopneumonia.* cell antigen while placebo vaccinated control sera did not.

I. METABOLIC INHIBITION TEST

In order to determine whether antibodies present in sera from swine vaccinated with Protein C had any direct inhibitory effect on *M. hyopneumoniae* cell growth, a metabolic inhibition test was performed. Vaccinated pig serum was substituted for specific-pathogen free pig serum in Friis medium (See Example X-A), and growth of cells in the substituted medium was compared with that in normal medium. The change in color of the phenol red in the medium from red to yellow was monitored indicating acid production, a normal product of *M. hyopneumoniae* metabolism.

Serum from pigs vaccinated with placebo showed a slight inhibition in metabolism compared to the normal medium controls. However, serum from pigs vaccinated with natural Protein C, recombinant full length Protein C, or truncated Protein C, all strongly inhibited metabolism of *M. hyopneumoniae*, as indicated by delay or lack of color change in these tubes. Measurement of pH at the time when the normal media control had changed color (3 days for 100×dilution of inoculum) showed that acid production was substantially reduced in the Protein C vaccinates. The normal medium control was pH 6.7 while the average pH of 5 sera from each vaccinate group was 7.5, 7.6, and 7.5 for the natural, full length recombinant, and truncated Protein C's respectively. The placebo vaccinated control sera averaged ph 7.0. Normal uninoculated Friis medium is pH 7.5.

J. WESTERN BLOT ANALYSIS OF VACCINATED PIG SERA

Protein samples were separated by SDS-PAGE as described in Example X-B4 except that the gel was 0.75 mm in thickness and samples were reduced with 2.5 2-mercaptoethanol before loading. Proteins were transblotted to a nitrocellulose sheet (SCHLEICHER & SCHUELL, BA-83, 0.2 μm pore size) with a Polyblot transfer system (AMERICAN BIONETICS) using their recommended buffers, for 30 min. at 100 V. Non-specific binding was blocked with 1% bovine Serum Albumin (PENTEX, Fraction IV, MILES DIAGNOSTICS) in TBS (10 mM Tris, 0.5M NaCl pH 8.0). Primary antibody (sera from vaccinated pigs) was diluted 1:200 in TBS+0.2% TWEEN 20 (SIGMA) 4–16 hours at room temperature. Unbound antibody was washed off in TBS+ 0.2% TWEEN 20 (shaking 3×10 min., room temperature) Second antibody (Peroxides conjugated rabbit anti-swine IgG, CAPPEL) was bound in the same buffer for 2–4 hours at room temperature. Unbound antibody was washed off and the blot immersed in substrate (300 μm/ml 4-chloro-1-naphthol, 0.03% hydrogen peroxide, in TBS+ 10% methanol). The reaction was terminated by rinsing the blot in distilled water.

Results of these blots indicated that sera from pigs vaccinated with natural Protein C strongly bound to: 1) an 85 kd band in western blot lanes containing separated proteins from *E. coli* stain pT5T:M852-1, which expresses the full-length recombinant Protein C; and 2) a ~50 kd band in lanes containing proteins from *E. coli* strain pT5T:M851-B2B, which expresses the truncated Protein C. Both of these bands correspond to the recombinant Protein C products in these strains. Conversely, sera from pigs vaccinated with either of the recombinant Protein C's bind strongly to an 85 kd band in lanes containing *M. hyopneumoniae* extract 7S (see Example X-A3) which corresponds to Protein C.

K. HISTOLOGICAL ANALYSIS OF LESIONS IN VACCINATED PIGS

Samples of lung (from vaccine experiment #8905) were collected and evaluated microscopically for lesions of Mycoplasma pneumonia from three groups of 15 pigs (recombinant Protein C vaccinates, truncated Protein C vaccinates, and placebo vaccinates). A grossly non-involved sample of lung from each pig and one representative lesion were examined and graded microscopically except for one pig in which no lesion remained after sampling for IFA and culture.

Extensive lymphold hyperplasia around airways and associated vessels was confirmed microscopically in 9/15 placebo, 5/15 Protein C and 7/15 truncated Protein C vaccinates. Microscopic lesions of bronchointerstitial pneumonia were present in 11/15 placebo, 9/15 Protein C, and 7/14 truncated Protein C vaccinates. Bronchointerstitial pneumonia characterized by either acute (edema and neutrophils predominately) or chronic alveolitis (lymphocytes, plasma cells, macrophages and neutrophils) was confirmed in 11/15 placebo, 9/15 Protein C and 7/15 truncated Protein C vaccinates. There was no to limited background (1+) lymphoid hyperplasia and no evidence of bronchointerstitial pneumonia in the non-involved samples of lung examined.

In summary the trend was for microscopic lesions consistent with mycoplasmosis to be most numerous in placebo vaccinates which parallels the gross observations. In addition the acute alveolitis component of the bronchointerstitial pneumonia occurred with greatest frequency in the placebo compared to the recombinant Protein C.

XI. APPLICATIONS TO OTHER SPECIES.

*Mycoplasma hyopneumoniae* is the causative agent of enzootic pneumonia in swine. Other mycoplasmas cause similar respiratory diseases in other organisms. For example: *M. pneumoniae* in humans; *M. gallisepticum* in chickens; *M. bovis* in cattle; etc. It is very possible that surface proteins homologous to polypeptide C exist in these other Mycoplasmas that may be effective as vaccines against these infective agents. The genes encoding these homologous proteins could be isolated by using the gene for polypeptide C as a probe for DNA hybridization at low stringency to a recombinant DNA library made from another mycoplasma species. The recombinant library could be constructed like the pUC18 library described in Example VIII-A1, and the library screened with the R69 probe as described in Example VIII-A2 except under different stringency conditions. DNA hybridization could be carried out in low stringency conditions at 32° in 30% formamide, 5X SSPE, 1% SDS, 0.1% sodium pyrophosphate, 0.15 mg/ml tRNA, 0.125 mg/ml sonicated salmon sperm DNA. An initial wash could be carried out in the same buffer (minus probe, tRNA, and sonicated salmon sperm DNA) at 32° C. (3×10 min washes) and the filters exposed to X-ray film for autoradiography to reveal clones which hybridize to the probe. If these stringency conditions are too low, indicated by a large number of "positive" clones on the film, the filters could be washed under higher stringency conditions by raising the formamide concentration in 5% increments, and/or raising the wash temperature in 5° C. increments, with each increment being followed by exposure to film to determine the number of "positive" hybridizing clones. At some combination of stringency conditions, it should be possible to eliminate most of the background false "positives" and to be left with the true "positive" clones for further analysis.

Inserts from the newly isolated positives would have to be subcloned into sequencing vectors and sequenced (See Example VIII-B for procedures and general strategy). The amino terminus of the coding sequence and the reading frame could be determined by comparison with the sequence for the Protein C gene. Once the positions of any UGA codons was determined, changes in these codons and other modifications to facilitate expression could be done in the same general manner as described for the Protein C gene (See Example IX-A and IX-B). Expression, purification, and testing of these recombinant proteins would depend on the properties of the proteins (likely to be similar to polypeptide C, described in Example IX-C4, X-B, X-C, and X-D) and the animals being tested.

There is also the possibility that recombinant Protein C itself from *M. hyopneumoniae* might be protective against other species. The recombinant Protein C could be tested directly in vaccine trials with other animals subsequently challenged with the corresponding Mycoplasma species.

XII. POSSIBLE USE OF PROTEIN C FRAGMENTS OR PEPTIDES AS VACCINES OR DIAGNOSTICS.

The possibility exists that fragments of Protein C might be useful either as vaccines or for diagnostic purposes. Such fragments might be produced in a variety of ways: 1) cloning of a section of the Protein C gene into a recombinant expression vector and producing the fragment as a recombinant protein much as the truncated version of Protein C was produced. This could be done for any section or combination of sections of the protein; 2) digestion of recombinant Protein C with endoproteinases (such as Endoproteinase LysC or chymotrypsin as described in the generation of peptides for amino acid sequencing (See Example VIII-D3)) and purification of the digestion products by reverse phase chromatography or other chromatographic techniques; 3) chemical synthesis of peptides corresponding to sections of Protein C using a peptide synthesizer such as the APPLIED BIOSYSTEMS INC. Model 430A. This method would be most useful for shorter peptides (<30 amino acids in length), but should not be ruled out for larger peptides as well.

One method for choosing regions of the amino acid sequence of Protein C which are likely to be antigenic uses a computer program to scan the sequence for regions which are hydrophilic and likely to be exposed on the surface of the protein (Hopp & Woods, *Proc. Nat. Acad. Sci. U.S.A.*, 78: 3824–3828(1981)). However, since Protein C exhibits significant protection even as a denatured protein, other regions of the protein should not be ruled out. Any segment or combination of segments of the amino acid sequence of Protein C might potentially be effective as a vaccine or diagnostic.

A peptide fragment to be used as a vaccine would be required to elicit an immune response directed against the natural Protein C (when administered as a vaccine to swine, See Example X-E). Such a response could be detected by Western blot analysis, showing that serum from pigs vaccinated with the fragment(s) recognize an 85 kd protein band on Western blots containing Protein C. Also a cellular immune response directed against Protein C could be detected using a T-lymphocyte proliferation assay in a method analogous to that described by Schwartz et. al., *J. of Immunol.*, 115:1330 (1975).

A fragment to be used as a diagnostic should be recognized by sera from pigs infected with *M. hyopneumonia* in an analytical procedure such as the ELISA test See Example X-H.

It will be apparent to those skilled in the art that various modifications and variations can be made in the processes of the present invention. Thus, it is intended that the present invention cover the modifications and variations of this invention provided that they come within the scope of the appended claims and their equivalents.

What is claimed is:

1. An isolated DNA sequence encoding protein C, wherein the DNA sequence encodes the amino acid sequence shown by FIG. 6.

2. An isolated DNA sequence encoding protein C, wherein the DNA sequence encodes the amino acid sequence shown by FIG. 4.

3. An expression vector encoding the protein C of claim 1.

4. An expression vector encoding the protein C of claim 2.

5. A host cell containing the vector of claim 3.

6. A host cell containing the vector of claim 4.

* * * * *

UNITED STATES PATENT AND TRADEMARK OFFICE
CERTIFICATE OF CORRECTION

PATENT NO. : 5,459,048  
DATED : October 17, 1995  
INVENTOR(S) : Kuner et al.

Page 1 of 2

It is certified that error appears in the above-indentified patent and that said Letters Patent is hereby corrected as shown below:

On the Title page, under "Other Publications", delete "Beltz et al, Methods in Enzymology, vol. 100:266-285 (1983) "Isolation of Mutigem Families . . . by Hybridization . . ."." and insert therefor --Beltz et al., Methods in Enzymology, vol. 100:266-285 (1983) "Isolation of Multigene Families and Determination of Homologies by Filter Hybridization Methods"--.

In the Specification

Col. 28, line 59, delete "5' GGGAAATTTTGTTTTCCAACCAAG- and insert therefor --5' GGGAAATTTTGTTTTCCAACCCAAG- --.

Line 62, delete "5' GATCTTCGTCTTGGAGTTGACTCAACT- and insert therefor --5' GATCTTCGTCTTGGAGTTGACTCCAACT- --.

UNITED STATES PATENT AND TRADEMARK OFFICE
CERTIFICATE OF CORRECTION

PATENT NO. : 5,459,048
DATED : October 17, 1995
INVENTOR(S) : Kuner et al.

It is certified that error appears in the above-indentified patent and that said Letters Patent is hereby corrected as shown below:

In the Claims

Col. 42, claim 2, lines 26-28, delete "wherein the DNA sequence encodes the amino acid sequence shown by FIG. 4" and insert therefore " wherein the DNA sequence encodes the amino acid sequence shown by FIG. 4" .

Signed and Sealed this

Fourteenth Day of May, 1996

Attest:

BRUCE LEHMAN

*Attesting Officer*   *Commissioner of Patents and Trademarks*